United States Patent [19]
Cole et al.

[11] Patent Number: 6,031,093
[45] Date of Patent: Feb. 29, 2000

[54] SOLID SALTS OF CLAVULANIC ACID

[75] Inventors: Martin Cole, Dorking; Thomas T Howarth, Rudwick; Christopher Reading, Southwater, all of United Kingdom

[73] Assignee: SmithKline Beecham p.l.c., United Kingdom

[21] Appl. No.: 08/417,628

[22] Filed: Apr. 6, 1995

Related U.S. Application Data

[63] Continuation of application No. 07/749,482, Aug. 15, 1991, which is a continuation of application No. 07/210,339, Jun. 23, 1988, abandoned, which is a continuation of application No. 05/569,007, Apr. 17, 1975, abandoned.

[51] Int. Cl.⁷ .................. C07D 503/18; C12P 17/18; A61K 31/42
[52] U.S. Cl. ............................................ 540/349
[58] Field of Search ........................ 514/210; 540/347, 540/348, 349

[56] References Cited

U.S. PATENT DOCUMENTS 4,526,783 7/1985 Cole et al. .......................... 424/114

FOREIGN PATENT DOCUMENTS 1315177  4/1973  United Kingdom .

*Primary Examiner*—Mark L Berch
*Attorney, Agent, or Firm*—Janice E. Williams; Charles M. Kinzig

[57] ABSTRACT

A new antibacterially active agent has been isolated from *Streptomyces clavuligerus*. This new compound which is designated clavulanic acid has the formula (I):

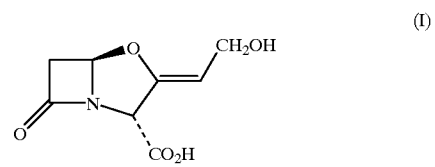

In addition to being a broad spectrum antibiotic of medium potency, clavulanic acid and its salts and esters have the ability to enhance the effectiveness of β-lactam antibiotics against many β-lactamase producing bacteria.

1 Claim, 1 Drawing Sheet

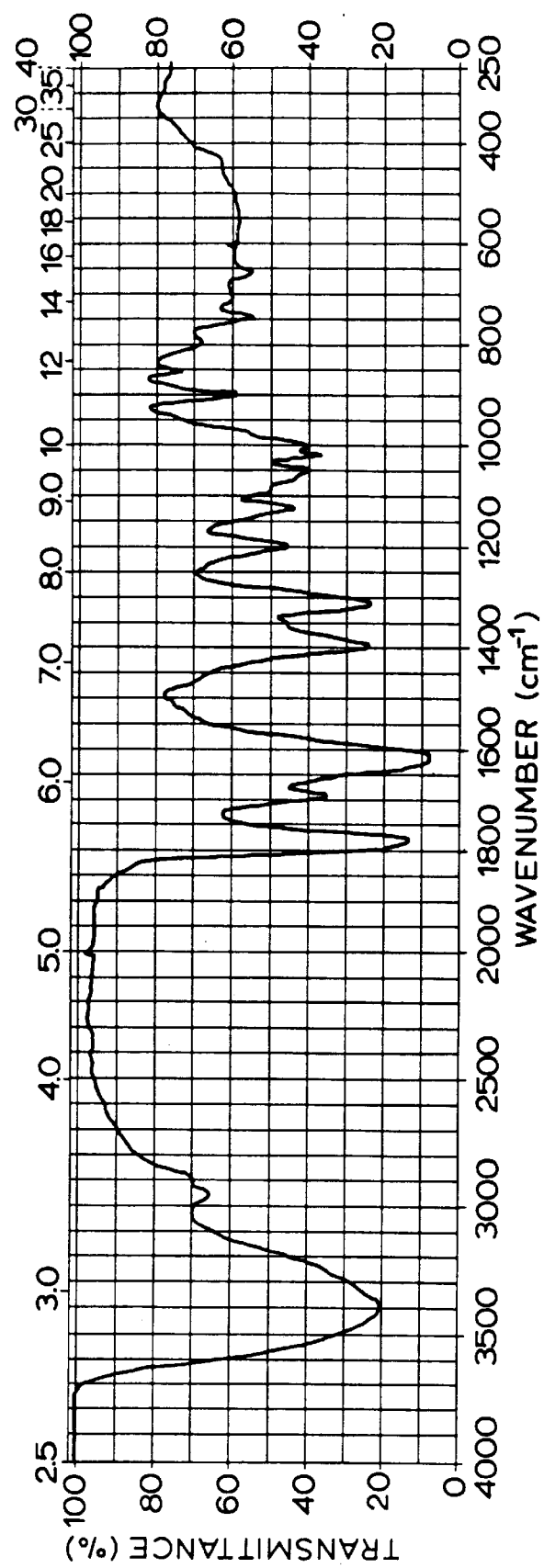

SOLID SALTS OF CLAVULANIC ACID

This is a continuation of application Ser. No. 07/749,482, filed Aug. 15, 1991, which was a continuation of Ser. No. 07/210,339, filed Jun. 23, 1988, now abandoned, which was a continuation of Ser. No. 05/569,007, filed Apr. 17, 1975, now abandoned.

BACKGROUND TO THE INVENTION a. *Streptomyces clavuligerus* has been described in detail by Higgens et al, *Int. J. Systematic Bacteriology*, 21, 326 (1971). This streptomycete was of interest because it produced certain β-lactam antibiotics such as penicillin N, 7-(5-amino-5-carboxyvaleramido)-3-carbamoyloxymethyl-3-cephem-4-carboxylic acid and 7-(5-amino-5-carboxyvaleramido)-3-carbamoyloxymethyl-7-methoxy-3-cephem-4-carboxylic acid. The streptomycete has been deposited in the Agricultural Research Service Collection as NRRL 3585 and in the American Type Culture Collection as ATCC 27064. *Streptomyces clavuligerus* has also been referred to in U.S. Pat. No. 3,770,590 and also by Nagarajen et al, *J. Amer. Chem. Soc.*, 93, 2308 (1971), Brannon et al, *Antimicrob. Agents Chemother.*, 1, 237 (1972) and *Antimicrob. Agents Chemother*, 1, 247 (1972) and Higgens et al, *J. Antibiotics*, 27, 298 (1974).

b. β-lactamases are enzymes which open the β-lactam ring of penicillins and cephalosporins to give products which are devoid of antibacterial activity. These enzymes are produced by many bacteria, notably species or strains of Escherichia, Klebsiella, Proteus, Pseudomonas, Enterobacter and Staphylococcus and are in many instances the explanation for the resistance of certain strains of such organisms to some penicillins and cephalosporins. The importance of β-lactamase production may be understood when it is realised that a high proportion of clinically isolated organisms produce β-lactamases (see, for example, M. Wilson and I. A. Freeman, *Bacteriological Proceedings*, 80 (1969) where in a paper entitled 'Penicillin Inactivation by Gram-negative Bacilli' they showed that 84%of the gram-negative organisms isolated in an American hospital produced β-lactamase). In many cases, some penicillins or cephalosporins are ineffective in treating diseases ascribed to non β-lactamase-producing organisms because of the common occurrence of co-infection by a β-lactamase producer (see, for example, R. May et al; *Brit. J. Dis. Chest.*, 66, 185 (1972). Combination of a β-lactamase inhibiting substance with a penicillin or cephalosporin might be expected to protect the latter from degradation by bacterial β-lactamase and thereby enhance their antibacterial activity against many infective organisms. This process of enhancement of the antibacterial activity is called synergism when the antibacterial activity of the combination is well in excess of the simple addition of the activities of the two separate substances. The β-lactamase inhibiting component of the mixture is referred to as a synergist and such substances are valuable for increasing the antibacterial activity of penicillins and cepalosporins against resistant organisms. It is one of the objects of this invention to provide such synergists.

c. Examples of the use of certain β-lactamase resistant semi-synthetic penicillins and cephalosporins as β-lactamase inhibitors and synergists for penicillins and cephalosporins have already been described in the literature, see for example, Sutherland et al., *Nature*, 201, 868 (1964); Sabath et al., *Nature*, 204, 1066 (1964); O'Callaghan et al., *Antimicrob. Agents and Chemotherapy*, 1968, 67 (1969). However, none of these known agents have a dramatic effect on the spectrum of the other antibiotic present in the mixture.

d. Certain actinomycete cultures have been described as producing β-lactamase inhibiting substances which act synergistically with penicillins or cephalosporins, for example, those cultures disclosed in British Patent No. 1,363,075 and those described by Hata et al, *J. Antibiotics*, 25, 473 (1972) and Umezawa et al, *J. Antibiotics*, 26, 51 (1973). None of these β-lactamase inhibitors of actinomycetal origin have yet been found to be of use in the clinic. Particularly noteworthy features which distinguish clavulanic acid from other β-lactamase inhibitors of actinomycetal origin are its extractability into organic solvents from culture filtrate at pH2, its high stability in human blood and its broad spectrum of anti-bacterial and β-lactamase inhibiting activity, its low molecular weight and its high $R_f$ values on paper chromatography using a variety of solvent systems.

DESCRIPTION OF THE INVENTION

We have discovered that the aerobic cultivation of *Streptomyces clavuligerus* in conventional nutrient media at about 25–30° C. under roughly neutral conditions produces a β-lactamase inhibitory substance which also possesses antibacterial activity. We have designated this new material 'clavulanic acid'.

Clavulanic acid has the following properties:

(a) It is a carboxylic acid.

(b) It forms a sodium salt which has a characteristic infra-red spectrum substantially as shown in the drawing.

(c) It is able to inhibit the growth of strains of *Staphylococcus aureus*.

(d) It is able to synergise the antibacterial effect of ampicillin against β-lactamase producing strains of *Escherichia coli, Klebsiella aerogenes* and *Staphylococcus aureus*.

(e) It is able to synergise the antibacterial effect of cephaloridine against the β-lactamase producing stains of *Proteus mirabilis* and *Staphylococcus aureus*.

(f) It forms a methyl ester which has a molecular weight (by mass spectroscopy) of 213.0635 which corresponds to the formula $C_9H_{11}NO_5$.

This clavulanic acid may be regarded as a monobasic carboxylic acid of the formula $C_8H_9NO_5$ which in the form of its sodium salt has a characteristic infra-red absorption spectrum substantially as shown in the drawing.

The compound produced by *Streptomyces clavuligerus* which has the above properties has the formula (II):

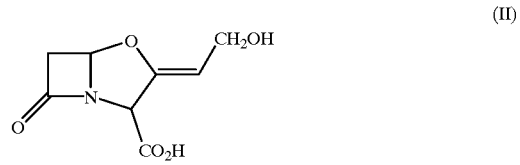

Thus clavulanic acid may be named 3-(β-hydroxyethylidene)-7-oxo-4-oxa-1-azabicyclo[3,2,0]heptane-2-carboxylic acid.

The stereochemistry at $C_5$ and $C_2$ of the clavulanic acid is the same as that found in naturally occurring penicillins and cephalosporins so that clavulanic acid may be represented by the structural formula (I):

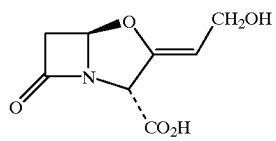
(I)

Thus a fuller chemical name for clavulanic acid is Z-(2R, 5R)-3-(β-hydroxyethylidene)-7-oxo-4-oxa-1-azabicyclo[3,2,0]heptane-2-carboxylic acid.

The great usefulness of clavulanic acid may be readily appreciated when it is realised that certain strains of *Klebsiella acrogenes* A, the growth of which is not inhibited by the presence of 125 μg/ml. of ampicillin, amoxycillin, carbenicillin or benzyl penicillin or by the presence of 10 μg/ml. of clavulanic acid, are inhibited by the presence of less than 12.5 μg/ml. of the previously mentioned penicillins when 5 μg/ml. of clavulanic acid is also present. Similar results have been observed for combinations containing various esters of clavulanic acid. For example, strains of *Klebsiella aerogenes* A, the growth of which is not inhibited by 125 μg/ml. of ampicillin, or by 10 μg/ml of clavulanic acid methyl ester are inhibited by less than 12.5 μg/ml. of ampicillin in the presence of 5 μg/ml. of the clavulanic acid methyl ester. It has also been found that strains of *Staphylococcus aureus* Russell, the growth of which is not inhibited by the presence of 100 μg/ml. of ampicillin or by 5 μg/ml of clavulanic acid, are inhibited by the presence of less than 10 μg/ml. of ampicillin in the presence of 1 μg/ml. of clavulanic acid. In tests on female mice, it has been found that blood and tissue levels of clavulanic acid considerably in excess of 5 μ/ml. can readily be achieved by subcutaneous administration of 100 mg/kg of the sodium salt of clavulanic acid and that useful levels of clavulanic acid can be obtained after oral administration of 100 mg/kg of the sodium salt of clavulanic acid.

Accordingly, the present invention provides clavulanic acid as hereinbefore described and its salts and esters.

Most suitably the salts of clavulanic acid will be pharmaceutically acceptable salts such as the sodium, potassium, calcium, magnesium, aluminium, ammonium and substituted ammonium salts such as the trimethylammonium, benzathine, procaine and like salts conventionally formed with penicillins or cephalosporins. Non-pharmaceutically acceptable salts of clavulanic acid are also included within the scope of this invention as they are useful intermediates in the preparation of esters of clavulanic acid, for example, the lithium or silver salts of clavulanic acid may be reacted with benzyl bromide to form the useful benzyl ester of clavulanic acid.

Salts of clavulanic acid tend to be more stable than the parent acid per se and thus form a favoured aspect of this invention. Particularly suitable salts of clavulanic acid include the sodium and potassium salts which have the formula (III) and (IV) respectively:

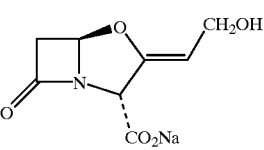
(III)

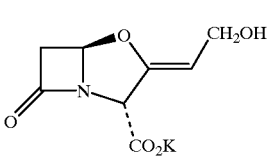
(IV)

Crystalline forms of such salts may contain water of hydration.

Suitable esters of clavulanic acid include those notionally derived from alcohols such as methanol, ethanol, propanol, butanol, 2,2,2-trichloroethanol, 2,2,2-trifluoroethanol, benzyl alcohol, p-nitrobenzyl alcohol, phenol, acetoxymethanol, pivaloyloxymethanol, 2-dimethylaminoethanol and other conventional alcohols. Various esters of clavulanic acid are useful intermediates in certain processes for the purification of clavulanic acid. Many clavulanic acid esters are useful synergistic compounds. The activity of such esters might be due to hydrolysis of the ester to the parent acid.

When used herein the term ester includes esters notionally derived from an alcohol or thiol of the formula ROH or RSH where R is an organic residue. Suitable groups R include alkyl, alkenyl, alkynyl, aryl, arylalkyl or other similar groups any of which may be substituted if desired. In order not to increase the molecular weight to an unreasonable extent, groups R do not normally include more than 16 carbon atoms, more suitably, not more than 12 carbon atoms and most suitably, not more than 8 carbon atoms.

Preferably, the group R is notionally derived from an alcohol ROH or (less favourably) a thiol RSH which is pharmaceutically acceptable.

Suitable substituents which may be included in the group R include halogen atoms and lower alkoxyl, hydroxyl, lower acyloxyl, lower alkylamino, lower dialkylamino and like groups. The term 'lower' means that the group contains up to 6 carbon atoms, and preferably up to 4 carbon atoms. Thus, for example, R may be a methyl, ethyl n-propyl, iso-propyl, straight or branched butyl, pentyl, heptyl, octyl, nonyl, decyl, undecyl, dodecyl, vinyl, allyl, butenyl, cyclopropyl, cyclobutyl, cyclopentyl, cyclohexyl, cycloheptyl, cyclohexenyl, cyclohexadienyl, methylcyclopentyl, methylcyclohexyl, benzyl, benzhydryl, phenylethyl, napthylmethyl, phenyl, naphthyl, propynyl, tolyl, 2-chloroethyl, 2,2,2-trichloroethyl, 2,2,2-trifluoroethyl, acetylmethyl, benzoylmethyl, 2-methoxyethyl, 2-dimethylaminoethyl, 2-diethylaminoethyl, 2-piperidinoethyl, 2-morpholinoethyl, 3-dimethylaminopropyl, p-chlorobenzyl, p-methoxybenzyl, p-nitrobenzyl, p-bromobenzyl, m-chlorobenzyl, 6-methoxynaphthyl-2-methyl, p-chlorophenyl, p-methoxyphenyl or any like group as well as those groups which are known from the penicillin or cephalosporin arts to produce esters known to be readily hydrolysed in vivo to the parent antibiotic.

Readily hydrolysable esters include, but are not limited to, those of the formulae (V) and (VI):

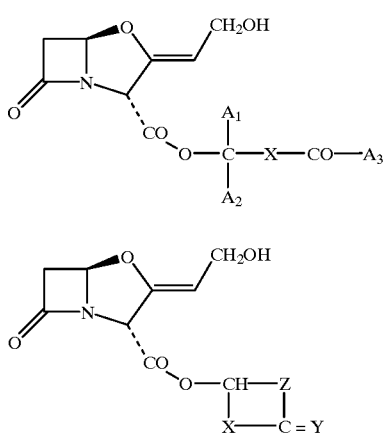

(V)

(VI)

wherein $A_1$ is a hydrogen atom, alkyl, aryl or aralkyl group; $A_2$ is a hydrogen atom or methyl group; $A_3$ is an alkyl, aryl or aralkyl group; X is oxygen or sulphur; Y is oxygen or sulphur and Z is a divalent organic group. Esters of the formulae (V) and (VI) which fairly readily release the clavulanic acid into the blood stream after administration include those wherein $A_1$ is a hydrogen atom, $A_2$ is a hydrogen atom or a methyl group and $A_3$ is a methyl, ethyl, propyl, butyl, benzyl, or phenyl group and those wherein X is oxygen, Y is oxygen and Z is —$CH_2CH_2$—, —CH:CH—,

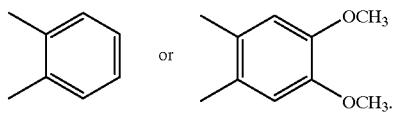

When used in conjunction with the preceding formula the term 'alkyl' includes alkyl of up to six carbon atoms; the term 'aryl' includes phenyl, naphthyl or phenyl substituted by an inert substituent such as a fluorine or chlorine atom or a methyl or methoxyl group or the like; when used herein the term 'aralkyl' means an alkyl group substituted by an aryl group.

Particularly suitable esters of the formulae (V) and (VI) include those of the formulae (VII) and (VIII):

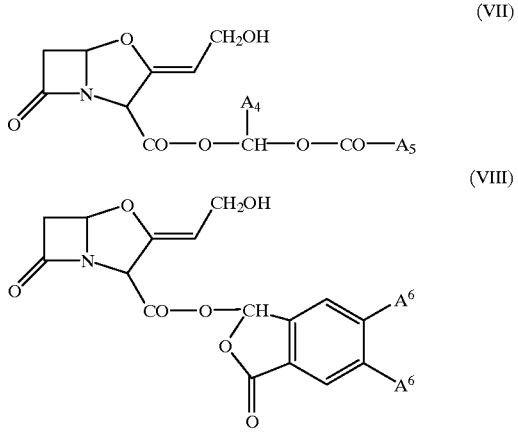

wherein $A_4$ is a hydrogen atom or a methyl group, $A_5$ is a methyl, t-butyl or phenyl group and $A_6$ is a hydrogen atom or a methoxyl group.

Many esters of clavulanic acid differ from analogous esters of penicillins or cephalosporins in that they show an enhanced tendency to hydrolyse to clavulanic acid under mild conditions. Thus, for example, simple alkyl esters such as the methyl ester slowly hydrolyse to clavulanic acid in water buffered to pH7. Esters which undergo some hydrolysis under mild conditions are included within the formula (IX):

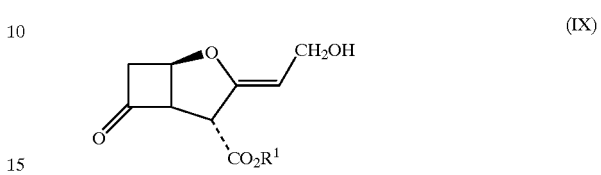

(IX)

wherein $R^1$ is a hydrocarbon group of 1–9 carbon atoms optionally substituted by halogen, lower alkoxy, lower acyl,/ hydroxyl, lower acyloxy/or optionally salted basic groups of the formula $NR^2R^3$ wherein $R^2$ is a hydrogen atom or a lower alkyl group, $R^3$ is a hydrogen atom or a lower alkyl group or is attached to $R^2$ so that $NR^2R^3$ is a 5- or 6-membered ring.

When used with reference to formula (IX) the term 'lower' means that the group contains 1–4 carbon atoms.

Suitably groups $R^1$ include alkyl and aralkyl groups optionally substituted by halogen, methoxyl, hydroxyl or salted $NR^2R^3$ groups wherein $R^2$ is a methyl or ethyl group and $R^3$ is a methyl or ethyl group or is joined to $R^2$ so that $NR^2R^3$ is a pyrrolidine, piperidine or morpholine group.

Most suitably alkyl groups $R^1$ are straight chain groups of up to 6 carbon atoms optionally substituted by one methoxyl, hydroxyl, salted $NR^2R^3$ group or one chlorine, bromine or iodine atom or by a $CCl_3$ or $CF_3$ group.

The esters of clavulanic acid of particular usefulnesses as synergists are those which hydrolyse in mammalian tissues, especially human blood, to yield clavulanic acid or a salt thereof because it is believed that clavulanic acid and its salts tend to be somewhat more useful synergistic agents than the esters per se. Many of the esters of the formulae (V)–(IX) are useful for this purpose.

A further group of particularly suitable esters of this invention are those useful intermediates which are readily converted to clavulanic acid or a salt thereof by chemical or biochemical techniques which are known from=the penicillin or cephalosporin arts to be sufficiently mild not to degrade reactive acid-labile β-lactam rings.

Most suitably, the ester is one removable by hydrogenolysis. Conventional esters for such a process include benzyl, substituted benzyl, benzhydryl, substituted benzhydryl, trityl and the like. The benzyl ester has proved particularly useful for this purpose.

By and large, the nature of any substituent in the ester moiety is unimportant as long as it does not interfere with the hydrogenolysis reaction.

Since clavulanic acid and its salts are useful intermediates in the preparation of the desirable antibacterially active esters of this invention, this invention also provides clavulanic acid and its salts when used as chemical intermediates.

As has been previously stated, clavulanic acid and its salts and esters have valuable therapeutic properties. Accordingly, in a further aspect, this invention provides a pharmaceutical composition which comprises clavulanic acid or a salt or ester thereof together with a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of the clavulanic acid or its salts are particularly suitable as high tissue levels of the compound of clavulanic acid can occur after administration by injection or infusion. Thus, one preferred composition aspect of this invention comprises clavulanic acid or a salt thereof in sterile form.

Unit dose compositions comprising clavulanic acid or a salt or ester thereof adapted for oral administration form a further preferred composition aspect of this invention.

Under certain conditions, the effectiveness of oral compositions of clavulanic acid and its salts and esters can be improved if such compositions contain a buffering agent or an enteric coating agent such that the compounds of the invention do not have prolonged contact with highly acidic gastric juice. Such buffered or enterically coated compositions may be prepared in accordance with conventional pharmaceutical practice.

The clavulanic acid or its salt or ester may be present in the composition as sole therapeutic agent or it may be present together with other therapeutic agents such as a β-lactam antibiotic. Suitable β-lactam antibiotics for inclusion in such synergistic compositions include not only those known to be highly susceptible to β-lactamases but also those which have a good degree of intrinsic resistance to β-lactamases. Thus, suitable β-lactam antibiotics for inclusion in the compositions of this invention include benzylpenicillin, phenoxymethylpenicillin, carbenicillin, methicillin, propicillin, ampicillin, amoxycillin, epicillin, ticarcillin, cyclacillin, 6-aminopenicillianic acid, 7-aminocephalosporanic acid, 7-aminodesacetoxycephalosporanic acid, cephaloridine, cephalothin, cefazolin, cephalexin, cefoxitin, cephacetrile, cephamandole, cephapirin, cephradine, cepaloglycine and other well known penicillins and cephalosporins or pro-drugs therefor such as hetacillin, metampicillin, the acetoxymethyl, pivaloyloxymethyl or phthalidyl esters of benzylpenicillin, ampicillin, amoxycillin or cephaloglycine or the phenyl, tolyl or indanyl α-esters of carbenicillin or ticarcillin or the like.

Naturally if the penicillin or cephalosporin present in the composition is not suitable for oral administration then the composition will be adapted for parenteral administration.

When present in a pharmaceutical composition together with a β-lactam antibiotic, the ratio of clavulanic acid or its salt or ester present to β-lactam antibiotic present may be from, for example 20:1 to 1:12, more usually 10:1.

The total quantity of antibacterial agents present in any unit dosage form will normally be between 50 and 1500 mg and will usually be between 100 and 1000 mg.

Compositions of this invention may be used for the treatment of infections of inter alia, the respiratory tract, the urinary tract and soft tissues in humans.

Compositions of this invention may also be used to treat infections of domestic animals such as mastitis in cattle.

Normally between 50 and 6000 mg of the compositions of the invention will be administered each day of treatment but more usually between 500 and 3000 mg. of the composition of the invention will be administered per day. However for the treatment of servere systemic infections or infections of particularly intransigent organisms, higher doses may be used in accordance with clinical practice.

The exact form of the compositions of this invention will depend to some extent on the micro-organism which is being treated. For treatment of most infections the compositions of this invention are normally adapted to produce a peak blood level of at least 0.1 µg/ml, more suitably at least 0.25 µg/ml, and preferably at least 1 µg/ml of synergist, for example, 2.5–5 µg/ml. of synergist.

The penicillin or cephalosporin sin synergistic compositions of this invention will normally be present by up to or at approximately the amount conventionally used when that penicillin or cepalosporin is the sole therapeutic agent used in the treatment of infection.

Particularly favoured compositions of this invention will contain from 150–1000 mg of amoxycillin, ampicillin or a pro-drug therefor and from 50–500 mg of clavulanic acid or a salt or in-vivo hydrolysable ester thereof and more suitably from 200–500 mg of amoxycillin, ampicillin or a pro-drug therefor and from 50–250 mg of clavulanic acid or a salt or in-vivo hydrolysable ester thereof.

The materials present in such compositions may be hydrated if required. The weights of the antibiotics in such composition are expressed on the basis of antibiotic theoretically available from the composition and not on the basis of the weight of pro drug.

When used herein the term "pro-drug" of an antibacterially active drug means any medicament which is known to be converted in the body to the antibacterially active drug per se.

This invention also provides a method of treating bacterial infection in a mammal which method comprises administering to the mammal an antibacterially effective amount of clavulanic acid or a salt or ester thereof.

Most suitably a pharmaceutically acceptable salt or in-vivo hydrolysable ester of clavulanic acid is uses.

This invention also provides a method of treating bacterial infection in a mammal, which method comprises administering to the mammal a synergistically effective amount of clavulanic acid or a salt or ester thereof and an antibacterially effective amount of a β-lactam antibiotic.

Most suitably a pharmaceutically acceptable salt or in-vivo hydrolysable ester of clavulanic acid is used.

A further aspect of this invention provides a method of treating infections in humans caused by *Klebsiella aeroginosa*, which method comprises administering to an infected human a daily dose of (a) at least 500 mg of ampicillin, amoxycillin or a pro-drug for ampicillin or amoxycillin, and (b) at least 100 mg of clavulanic acid or a salt or in-vivo hydrolysable ester thereof.

The penicillin and synergist may be administered in separate compositions or in synergistic compositions containing both components. Normally the daily dose of the antibiotics will be administered in divided form, for example, as 2 to 5 doses per day. Usually the antibiotics will be administered as 3 or 4 doses per day.

The penicillin used in this treatment may be anhydrous ampicillin, ampicillin trihydrate, sodium ampicillin, hetacillin, pivampicillin hydrochloride, talampicillin hydrochloride, amoxycillin trihydrate, sodium ampoxycillin or the like. Each unit dose will usually contain from 200–1000 mg of the penicillin, for example, 250 to 500 mg.

The synergist used in this treatment will generally be a salt or in-vivo hydrolysable ester of clavulanic acid such as the sodium or potassium salt of clavulanic acid or the acetoxymethyl, pivaloyloxymethyl, phthalidyl or like ester of clavulanic acid. Each unit dose will usually contain from 50 to 500 mg of the synergist, for example, 100 to 250 mg.

A further aspect of this invention provides a method of treating infections in humans caused by *Pseudomonas aeroginosa*, which method comprises administering to an infected human a daily dose of at least 1 g. of carbenicillin or ticarcillin or a pro-drug for carbenicillin or ticarcillin and (b) at least 0.5 g. of clavulanic acid or a salt or in-vivo hydrolysable ester thereof.

The penicillin and synergist may be administered in separate compositions or synergistic compositions containing both components. Normally, the daily dose of antibiotics will be administered in divided form, for example, as 2 to 5 doses per day. Usually the antibiotics will be administered as 3 or 4 doses per day. For systemic or several infections the compositions will be adapted for administration by injection or infusion. For infections of the urinary tract the compositions may be adapted for administration orally or by injection or infusion.

The penicillin used in this treatment may be carbenicillin, carbenicillin α-phenyl ester, carbenicillin α-5-indanyl ester, ticarcillin, ticarcillin α-tolyl ester, ticarcillin α-phenyl ester and like, and will usually be in the form of a salt such as a sodium salt. Each unit dose will usually contain from 400 to 4000 mg of the penicillin, for example, 500 to 1000 mg.

The synergist used in this treatment will suitably be the sodium or potassium salt of clavulanic acid or an in-vivo hydrolysable ester thereof, such as the acetoxymethyl, pivaloyloxymethyl or phthalidyl ester of clavulanic acid. Each unit dose will usually contain from 200 to 1000 mg of the synergist, for example, 250 to 750 mg.

A further aspect of this invention provides a method of treating infections in the respiratory tract of humans, which method comprises administering to an infected human a daily dose of (a) at least 500 mg of amoxycillin or ampicillin or a pro-drug for ampicillin or amoxycillin, and (b) at least 100 mg of clavulanic acid or a salt or in-vivo hydrolysable ester thereof.

Especially suitable doses and methods of administration are similar to those described for the treatment of infections due to *Klebsiella aeroginosa*.

A further aspect of this invention provides a method of treating infections in the urinary tract in humans which method comprises administering to an infected human a daily dose of (a) at least 500 mg of ampicillin, amoxycillin, carbenicillin, ticarcillin, cephalothin, cephaloridine, cephaloglycine, cephalexin, cefazolin, cephapirin or cephradine or cephradine or a pro-drug for such medicaments and (b) at least 100 mg of clavulanic acid or a salt or in-vivo hydrolysable ester thereof.

The medicaments may be administered in manner analogous to that described above for the treatment of infections due to *Klebsiella aeroginosa*.

In a process aspect, the present invention provides a process for the preparation of clavulanic acid and salts and esters thereof which process comprises cultivating a strain of *Streptomyces clavuligerus* and recovering clavulanic acid or a salt thereof from the culture medium and thereafter if desired, forming the free acid or a salt or ester by methods known per se.

Preferably, *Streptomyces clavuligerus* ATCC 27064 or a high yielding mutant thereof is used in the process of this invention.

When used herein, the term 'cultivation' means the deliberate aerobic growth of a clavulanic acid producing organism in the presence of assimilable sources of carbon, nitrogen and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined. In our hands we have found media containing complex nutrients such as yeast extract, soya bean flour and the like to be particularly suitable.

The nutrient media which may be used for the cultivation of *Streptomyces clavuligerus* may contain, in the range 0.1–10% a complex organic nitrogen source such as yeast extract, corn steep liquor, vegetable protein, seed protein, hydrolysates of such proteins, milk protein hydrolysates, fish and meat extracts and hydrolysates such as peptones. Alternatively chemically defined sources of nitrogen may be used such as urea, amides, single or mixtures of common amino acids such as valine, asparagine, glutamic acid, proline and phenylalanine. Carbohydrate (0.1–5%) may be included in the nutrient media but flucose in certain media is undesirable having a depressing effect on the yield of the desired clavulanic acid. Starch or starch hydrolysates such as dextrin, sucrose, lactose or other sugars or glycerol or glycerol esters may also be used. The source of carbon may also be derived from vegetable oils or animal fats. Carboxylic acids and their salts can be included as a source of carbon for growth and production of β-lactamase inhibitors. A particularly suitable low cost medium is one containing soya bean flour (Arkasoy) plus dried malt distillers solubles (Scotasol) plus dextrin.

The addition of antifoam agents such as Pluronic L81 may be necessary to control foaming of certain media in fermenters.

Mineral salts such as NaCl, KCl, $MgCl_2$, $ZnCl_2$, $FeCl_3$, $Na_2SO_4$, $FeSO_4$, $MgSO_4$ and $Na^+$ or $K^+$ salts of phosphoric acid may be added to the media described above particularly if chemically defined; $CaCO_3$ may be added as a source of $Ca^{++}$ ions or for its buffering action. Salts of trace elements such as nickel, cobalt or manganese may also be included. Vitamins may be added if desired.

When used herein the term 'mutant' includes any mutant strain which arises spontaneously or through the effect of an external agent whether that agent is applied deliberately or otherwise. Suitable methods of producing mutant strains include those outlined by H. I. Adler in Techniques for the Development of Micro-Organisms in 'Radiation and Radioisotopes for Industrial Micro-Organisms', Proceedings of a Symposium, Vienna, 1973, page 241, International Atomic Energy Authority and these include:

i. Ionising radiation (such as X- and X-rays), UV light, UV light plus a photosensitizing agent (such as 8-methoxypsoralen), nitrous acid, hydroxylamine, pyrimidine base analogues (such as 5-bromouracil), acridines, alkylating agents (such as mustard gas, ethylmethane sulphonate), hydrogen peroxide, phenols, formaldehyde, heat, and
  ii. Genetic techniques such as recombination, transformation, transduction, lysogenisation, lysogenic conversion and selective techniques for spontaneous mutants.

cultivation of *Streptomyces clavuligerus* normally takes place in the temperature range 15–40° C., usually 20–35° C. and preferably, 25–30° C. and at a pH of between 5 and 8.5, preferably between 6 and 7.5.

The *Streptomyces clavuligerus* may be cultivated in the above media in glass conical flasks aerated by shaking on a rotary shaker or in baffled stainless steel fermenters stirred with vaned disc impellers and aerated with a sparger. The fermentation may also be carried out in a continuous fashion.

The starting pH of the fermentation is typically 7.0 and maximum yield of clavulanic acid is obtained in 2–10 days at 20–35° C. In a stirred stainless steel fermenter using the Arkasoy/Scotasol/Dextrin medium referred to above the preferred temperature is 26° C. and peak yields clavulanic are obtained within 5 days.

Clavulanic acid may be extracted from culture filtrate by a variety of methods. Solvent extraction from cold culture filtrate adjusted to acid pH values and methods based on the anionic nature of the metabolite such as the use of anion exchange resins have been found to be particularly useful. The cells of the *Streptomyces clavuligerus* are normally first removed from the fermentation by filtration or centrifugation before such extraction procedures are commenced.

In the solvent extraction process, the culture filtrate is chilled and the pH lowered into the region of pH 2–3 by the addition of acid while thoroughly mixing with a water immiscible organic solvent such as n-butylacetate, methylisobutylketone, n-butanol or ethylacetate. The acid used to lower the pH of the medium is normally a mineral acid such as hydrochloric, sulphuric, nitric, phosphoric or the like acid. n-Butanol is a particularly suitable solvent for use in the extraction of the acidified culture filtrate. After separation of the phases by centrifugation, the β-lactamase inhibiting metabolite is back extracted from the solvent phase into aqueous sodium bicarbonate or potassium hydrogen phosphate buffer, $CaCO_3$ suspension or water while maintaining the pH at approximate neutrality, for example, at pH 7.0. This aqueous extract after separation of phases may be concentrated under reduced pressure and freeze dried to give a crude preparation of a salt of clavulanic acid. This preparation is stable when stored as a dry solid at −20° C.

In the anion exchange resin process, the clarified culture filtrate at an approximately neutral or slightly acid pH, for example pH 6–7, is percolated down a column of weak or strong base anion exchange resin such as Amberlite IR4B or Zerelite FFIF respectively until the resins is saturated and the β-lactamase inhibiting material emerges from the bottom. The column is then washed with water and eluted with aqueous sodium chloride. The β-lactamase inhibiting fractions are collected, bulked, desalted and freeze dried to yield a crude solid salt of clavulanic acid. Amberlite IR4B is an example of a weakly basic anion exchange resin with polyamine active groups and cross linked polystyrene-divinyl-benzene matrix. Zerolite FFIP is a strongly basic anion exchange resin with quaternary ammonium active groups and a cross linked polyvinyl-divinylbenzene matrix. Resins similar to Zerolite FFIP include Isopor FFIP and DeAcidite FFIP SRA.64. These resins were supplied by BDH Chemicals Ltd., Poole, Dorset, U.K.

An alternative form of the extraction process is to contact the culture filtrate (usually at approximately neutral pH) containing a salt of clavulanic acid, with an organic phase in which is dissolved a water insoluble amine. Suitable organic solvents include such conventional water immiscible polar solvents as methylisobutylketone, trichloroethylene and the like. Suitable amines include secondary or tertiary amines in which one of the substituent groups is a long chain aliphatic group, for example, of 12–16 carbon atoms and the other is a tertiaryalkyl group so that the molecule is lipophilic. In our hands Amberlite LA2 has proved a successful amine. Normally the amine is used as its acid addition salt. After this extraction process the clavulanic acid is present in the organic phase as the amine salt. The organic phase is then separated from the culture filtrate. The clavulanic acid may be back extracted into an aqueous phase by back extraction with a salt solution, preferably a concentrated solution of sodium chloride, sodium nitrate or the like. The crude salt of clavulanic acid may then be obtained by freeze drying or the like.

Other primary methods of isolation which may be used include conventional methods such as adsorption onto carbon, precipitation, salting out and molecular filtration but these methods are not usually as successful as the above described methods which are preferred.

Further purification of the crude solids obtained by methods described above may be obtained by a variety of methods but ion exchange column chromatography is particularly suitable especially when using Isopride Acidite FFIP SRA64 or DEAE cellulose. The DeAcidite column may be gradient eluted with aqueous solution of a salt such as sodium chloride (0–0.5 M). The column of DEAE cellulose in 0.01 M phosphate buffer at pH7 may be eluted with a salt solution, normally a NaCl solution (0–0.2 M NaCl in 0.01 M phosphate buffer pH7). Active fractions may be detected by their β-lactamase inhibitory activity and their antibacterial activity against *Klebsiella aerogenes* in an agar diffusion assay. The fractions containing the bulk of this activity are then combined and concentrated to a small volume under vacuum. This crude preparation of the clavulanic acid salt is desalted by percolating down a column of Bio Gel P2.

(Bio Gel P2 is an example of a highly lipophilic resin onto which organic materials may be adsorbed but which does not retain inorganic salts. Bio Gel P2 is a polyacrylamide gel supplied by Bio Rad, 32nd and Griffen Avenue, Richmond, Calif. 94804, USA). The active desalted material is then concentrated, mixed with ethanol and further chromatographed on a cellulose column using butanol/ethanol/water 4/1/5 v/v top phase, as solvent.

Fractions containing material which inhibit *Escherichia coli* β-lactamase are bulked, evaporated to dryness under vacuum, redissolved in water and freeze dried to give a salt of clavulanic acid as a white solid.

The methods we have found most useful in detecting clavulanic acid in culture filtrates are paper chromatography and a bioautographic detection system. Clavulanic acid may be assayed by making use of its β-lactamase inhibiting activity. Thin layer chromatography may be used to detect clavulanic acid in solid preparations. These detection and assay procedures are described hereinafter.

A variation of the process for the preparation of a pure form of clavulanic acid or its salts comprises isolating an impure form of clavulanic acid or salt thereof, forming an ester of clavulanic acid in conventional manner, purifying the ester and thereafter regenerating clavulanic acid or a salt thereof from the ester.

The impure clavulanic acid or its salts used in this process will normally contain at least 1% by weight of the antibiotic.

Suitable esters for use in this process include those which may be cleaved by hydrogenolysis, enzymatic methods or by hydrolysis under very mild conditions.

One suitable group of esters used in this process is that of the formula (X):

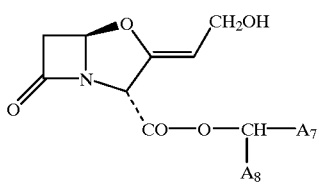

(X)

wherein $A_7$ is a hydrogen atom or an optionally substituted phenyl group and $A_8$ is an optionally substituted phenyl group.

Most suitably $A_7$ is a hydrogen atom or a phenyl, tolyl, chlorophenyl or methoxyphenyl group and $A_8$ is a phenyl, tolyl, chlorophenyl or methoxyphenyl group.

Preferably $A_7$ is a hydrogen atom and $A_8$ is a phenyl group.

The esters of formula (X, may be cleaved by hydrogenolysis to yield clavulanic acid or salt thereof.

Other groups of esters which may be used in this process include those of formulae (V) and (VI) as hereinabove described. Such esters may be converted to salts of clavulanic acid by mild alkaline hydrolysis, for example, at pH 7.5.

The impure form of clavulanic acid or salt thereof which is to be purified in this process may be in the form of a solid or solution which will usually also contain considerable quantities of organic or inorganic impurities.

The clavulanic acid or salt thereof may be converted into an ester by the esterification reactions referred to hereinafter. The preferred method of forming the required ester of clavulanic acid is by the reaction of a salt of clavulanic acid with an esterifying agent such as a reactive halide, sulphonate ester or the like as hereinafter described. Such reactions are frequently carried out in an organic solvent of high dielectric constant such as dimethylformamide, dimethylformamide/acetone, dimethyl-sulphoxide, N-methylacetamide, hexamethylphosphoramide and the like.

If desired the salt of clavulanic acid may be dissolved in the solvent in conventional manner or it may be bound to a polymeric support. Suitable supports for use in this process include strong base anion exchange resins, especially those possessing a macroreticular nature which permits the use of non-aqueous solvent systems. We have found Amerblyst A26 to be suitable for this purpose. The clavulanic acid salt may be adsorbed onto the resin from the culture filtrate and the resin then suspended in dimethylformamide containing sodium iodide or alternatively eluted columnwise with a solution of sodium iodide in dimethylformamide or in a mixture of dimethylformamide and acetone.

Once formed, the impure ester of clavulanic acid is normally purified chromatographically. In such procedures the ester is normally dissolved in an organic solvent such as ethylacetate, methylene chloride, chloroform, cyclohexane or similar solvents. The solid phase used in the chromatographic process is normally an inert material such as silica gel or chromatographically similar materials.

The fractions emerging from the column may be tested for the presence of the clavulanic acid by making use of its synergistic properties. Active fractions are normally combined and the organic solvent evaporated off under reduced pressure.

The ester resulting from this process is generally of acceptable purity, but the material may be re-chromatographed if desired.

This purified ester of clavulanic acid may be converted to clavulanic acid or a salt thereof by the before mentioned methods.

A particularly suitable method of obtaining clavulanic acid or its salt is by hydrogenation of a compound of the formula (X) as hereinbefore described. Such reactions normally take place in the presence of a transition metal catalyst using low or medium pressures of hydrogen. The reaction may be carried out at high, ambient or depressed temperatures, for example at 0–100° C. Particularly suitable reaction conditions for such hydrogenations will use a slightly superatmospheric pressure of hydrogen at an approximately ambient (12–20° C.) temperature. The reaction may be carried out in conventional solvents such as lower alkanols, for example, ethanol. We have found that a particularly suitable catalyst is palladium on charcoal.

If the hydrogenation is carried out in the presence of a base then a salt of clavulanic acid is produced, for example, the sodium or potassium salts result if the reaction is carried out in the presence of sodium or potassium hydrogen carbonate.

The clavulanic acid or salt thereof resulting from such reactions is generally of good purity.

Esters or clavulanic acid may be prepared by the esterification of clavulanic acid or a salt thereof by conventional methods.

Suitable methods of ester formation include (a) reaction of a salt of the acid of clavulanic acid with a compound of the formula Q–R where Q is a readily displaceable group and R is an organic group; (b) the reaction of clavulanic acid with an diazoalkane and (c) the reaction of clavulanic acid with an alcohol ROH in the presence of a condensation promoting agent such as carboiimide or the like.

Suitable salts of clavulanic acid which may be reacted with compounds R–Q include alkali metal salts such as the sodium or potassium salts or other conventional salts such as the silver salt Suitable groups Q include those atoms or groups known to be displaceable by carboxylate anions and include chlorine, bromine and iodine atoms, sulphonic acid esters such as the $O.SO_2CH_3$ or $O.SO_2C_6H_4CH_3$ groups, active ester groups such as the $O.CO.H$ or $O.CO.CF_3$ group and other conventional groups displaceable by nucleophiles.

The preceding reaction is normally carried out in an organic solvent of relatively high dielectric constant such as dimethylformamide, acetone, dioxane, tetrahydrofuran or the like and at a non-extreme temperature such as –5° C. to 100° C., more usually +5° C. to 30° C., for example at ambient temperature.

The reaction of clavulanic acid with a diazocompound is a mild method of making alkyl, aralkyl or similar esters. The diazotization reaction may be performed under conventional reaction conditions, for example at a non-extreme temperature and in a conventional solvent. Such reactions are normally carried out at between about –5° C. and 100° C., more usually from 5° C. to 30° C., for example at ambient temperature. Suitable solvents for this reaction include lower alkanols such as methanol and ethanol and solvents such as tetrahydrofuran, dioxane and the like. Ethanol has proved a particularly useful solvent for this reaction.

The reaction of clavulanic acid with an alcohol or thiol in the presence of a condensation promoting agent will normally take place in an inert organic solvent of relatively high dielectric constant such as acetonitrile This reaction is usually carried out at an ambient or depressed temperature, for example at –10° C. to +22° C., more usually –5° C. to 18° C., for example initially at 0° C. and thereafter gradually warming to about 15° C. The condensation promoting agent used is normally one which removes water from the reaction mixture. Suitable agents include carbodiimides, carbodiimidazoles or equivalent reagents. Dichyclohexylcarbodiimide has proved to be a particularly suitable condensation promoting agent for use in this process. In order to minimise self condensation of the clavulanic acid, this reaction is usually carried out in the presence of a considerable excess of the alcohol or thiol.

Other suitable methods of ester formation include (d) removal of the elements of carbon dioxide from a compound of the formula (XI)

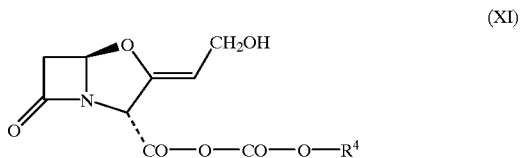

(XI)

where $R^4$ is an inert organic group; and (e) reaction of a compound of the formula (XI) with an alcohol ROH (or less favourably with a thiol RSH).

The elements of carbon dioxide may be removed from the compound of formula (XI) spontaneously during its preparation or alternatively by heating the compound of the formula (XI) in an inert solvent. Suitable inert solvents include ether solvents such as diethylether, tetrahydrofuran, dioxane and the like. In many cases the compound of the formula (XI) decomposes spontaneously even at a depressed temperature, for example, at −5° C., to yield an ester of the formula

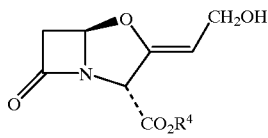

wherein $R^4$ is an inert group within the definition of R.

When the compound of the formula (XI) is to be reacted with an alcohol (or less favourably with a thiol) then this reaction is normally carried out in an inert solvent such as an ether solvent in the presence of an excess of the alcohol (or thiol) in order to prevent self-condensation of the clavulanic acid derivative.

Such methods of esterification are not in general as useful as those involving reaction of a salt of clavulanic acid with R——Q as herinbefore described.

The compound of the formula (XI) may be prepared by the reaction of a salt of clavulanic acid with $Cl.CO.O.R^4$ or the chemical equivalent thereof. Normally this reaction is carried out at a depressed temperature, for example, at a temperature not greater than 5° C., and in an inert solvent, for example diethylether, tetrahydrofuran, dioxane and the like. Most suitably the salt of clavulanic acid used in this reaction is a lipophilic salt so that it will dissolve in the solvent although if desired the less favourable sodium salt may be employed by suspending it in the fraction medium.

DESCRIPTION 1

Assay Suitable for Detection of Clavulanic Acid

Principle of the Assay

Solutions containing clavulanic acid (culture filtrate, samples from isolation procedure and the like) are incubated for 15 minutes with a β-lactamase preparation in 0.05M phosphate buffer at pH 7 and 37° C. During this time, enzyme inhibition or inactivation occurs. Substrate (benzylpenicillin) is then added and incubation continued for 30 minutes at 37° C. The amount of enzymic degradation of the substrate to penicilloic acid is determined by the hydroxylamine assay for penicillin. The amount of β-lactamase used is such as to give 75% hydrolysis of the benzylpenicillin in 30 minutes at 37° C.

The extent of hydrolysis is a reflection of the amount of enzyme remaining uninhibited. The results are expressed as per cent inhibition of the enzyme activity by a given dilution of the clavulanic acid—containing solution (e.g. culture filtrate) or the concentration of clavulanic acid (μg/ml) giving 50% inhibition of the enzyme under the above stated conditions ($I_{50}$).

β-lactamase Enzyme

The β-lactamase produced by *Escherichia coli* JT4 is used as an enzyme. This culture is an ampicillin resistant strain and owes its resistance to the production of an R-factor controlled β-lactamase. Other similar R-factor controlled β-lactamases may be used if desired.

The culture maintained on nutrient agar slopes, is inoculated into 400 ml. of sterile Tryptone medium contained in a 2 liter conical flask. This medium has the following composition Tryptone (Oxoid) 32 g/l, yeast extract (Oxoid) 20 g/l, Nacl 5 g/l and $Cacl_2 6H_2O$ 2.2 g/l. The final pH was adjusted to 7.4 with dilute NaOH. The flask is shaken at 25° C. for 20 hours on a rotary shaker at 240 r.p.m.

The bacterial cells are collected by centrifugation, washed with 0.05M phosphate buffer pH 7 (resuspended and centrifuged) and resuspended in water to give cell concentration 25 times that in the cultivation medium. This cell suspension was then disrupted in an MSE ultrasonic disintergrator at 4° C. the cell debris was removed by centrifugation and aliquots of the supernatant stored deep frozen. For use in the assay procedure, the supernatant is diluted in 0.005M phosphate buffer until it gives about 75% hydrolysis of a 1 mg/ml. solution of benzylpenicillin in 30 minutes at 37° C.

Assay Procedure

Suitable dilutions of the inhibitor preparation and β-lactamase solution are mixed and incubated at 37° C. for 15 minutes (Test). A control with buffer in place of inhibitor preparation is also incubated. Benzylpenicillin solution (substrate) is then added to test and control mixtures, incubation continued for a further 30 minutes at 37° C. The residual benzylpenicillin in each mixture is then estimated using the hydroxylamine assay as described by Batchelor et al, *Proc. Roy. Soc., B* 154, 498 (1961). 6 ml. of hydroxylamine reagent are added to all tests, controls and blanks and are allowed to react for 10 minutes at room temperature prior to the addition of 2 ml of ferric ammonium sulphate reagent. The absorption of the final solutions is measured in an E.E.L. Colorimeter or a Spectrophotometer at 490 nm against the reagent blank. The composition of the reactions, tests and blanks prior to the hydroxylamine assay are as follows:

| Components (all dissolved in or diluted with 0.005M pH 7 phosphate buffer) | Test | Benzyl-penicillin Blank ml. | Control ml. | Reagent Blank ml. |
|---|---|---|---|---|
| *Escherichia coli* β-lactamase solution | 1.9 | 0.0 | 1.9 | 1.9 |
| Inhibitor solution | 0.1 | 0.0 | 0.0 | 0.0 |

-continued

| Components (all dissolved in or diluted with 0.005M pH 7 phosphate buffer) | Test | Benzyl-penicillin Blank ml. | Control ml. | Reagent Blank ml. |
|---|---|---|---|---|
| Benzylpenicillin 5 mg/ml. | 0.5 | 0.5 | 0.5 | 0.0 |
| 0.005M pH 7 phosphate buffer | 0.0 | 2.0 | 0.1 | 0.6 |

Calculation of Results

The percentage inhibition of the β-lactamase is calculated as follows—

Absorption of benzylpenicillin blank minus absorption of control (uninhibited reaction)=x Absorption of test (inhibited reaction) minus absorption of control (uninhibited reaction)=y $$\% \text{ inhibition} = \frac{y}{x} \times 100$$

To obtain the $I_{50}$ value, the inhibitor preparation is diluted until 50% inhibition of the β-lactamase inactivation of benzylpenicillin is obtained in the above procedure.

DESCRIPTION 2

Paper Chromatographic Detection of Clavulanic Acid

Culture filtrate and a reference solution of clavulanic acid (250 μg/ml partially purified preparation), are spotted (20 μl/origin) onto Whatman No1 paper strips 1 cm. wide. The chromatograms are run by descending chromatography for 16 hours at 5° C. using n-butanol/iso-propanol/water, 7/7/6 v/v as solvent. The strips are dried at 40° C. and laid on agar plates containing 6 μg/ml benzylpenicillin and seeded with a β-lactamase producing strain of *Klebsiella aerogenes* (synergism system). The plates are incubated overnight at 30° C. and clavulanic acid revealed as a zone of inhibited growth. The $R_f$ value of the zone was 0.46. The 6 μg/ml benzylpenicillin alone is below the concentration required to kill the *Klebsiella aerogenes* but in the presence of a β-lactamase inhibitor, this concentration becomes toxic, that is to say there is synergism.

Use of the above synergism system enables clavulanic acid to be detected at concentrations below those at which it shows antibacterial activity.

DESCRIPTION 3

Thin Layer Chromatographic Detection of Clavulanic Acid Sodium Salt

Solutions of clavulanic acid sodium salt preparations are spotted (5 μl of 1 mg/ml) onto glass plates coated with a 0.25 mm layer of silica gel (F254) as supplied by E. Merck, Darmstadt, Germany. The chromatograms are run at 22° C. using the top phase of the mixture n-butanol/ethanol/water 4/1/5 v/v. The chromatogram plates are dried at 40° C. and clavulanic acid sodium salt located by bioautography on agar plates containing 6 μg/ml. benzylpenicillin and seeded with *Klebsiella aerogenes* (synergism system—see section on paper chromatography above). The agar surface is covered by a fine filter cloth before laying the TLC plate onto it. After allowing 15–30 minutes for wetting and diffusion, the TLC plate is lifted off with the aid of the filter cloth and the agar plate incubated overnight at 30° C. to reveal the zones of inhibited growth. The $R_f$ value of clavulanic acid sodium salt in the above solvent is approximately 0.37. Two spray reagents, Ehrlich and triphenyltetrazolium chloride are also used to reveal the clavulanic acid sodium salt zone. The former reagent consists of 300 mg of p-dimethylaminobenzaldehyde dissolved in 9 ml. of ethyl alcohol, 54 ml. of n-butanol and 9 ml of concentrated HCl. On heating the sprayed TLC plate at 120° C. for 1–2 minutes, clavulanic acid sodium salt appears as a pink spot. The triphenyltetrazolium chloride reagent consists of a mixture of 1 volume of a 4% solution of this compound in methanol with 1 volume of methanolic sodium hydroxide. After spraying, the TLC plates are heated at 80° C. Clavulanic acid sodium salt appears as a red spot on a white background. solution

EXAMPLE 1

Cultivation of *Streptomyces clavuligerus*

*Streptomyces clavuligerus* was cultivated at 26° C. on agar slopes containing 1% Yeatex (yeast extract), 1% glucose and 2% Oxoid agar No.3, pH 6.8. A sterile loop was used to transfer mycelium and spores from the slope into 100 ml of a liquid medium in a 500 ml Ehrlenmeyer flask. The liquid medium had the following composition:

| Oxoid Malt Extract | 10 g/l |
|---|---|
| Oxoid Bacteriological Peptone | 10 g/l |
| Glycerol | 20 g/l |
| Tap water | 1 liter |

The medium was adjusted to pH 7.0 with sodium hydroxide solution and 100 ml. volumes dispensed into flasks which wore closed with foam plugs prior to autoclaving at 15 lb/sq.in. for 20 minutes. An inoculated seed flask was shaken for 3 days at 26° C. on a rotary shaker with 2 inch throw and a speed of 240 r.p.m. Production stage flasks containing the liquid medium described above were inoculated with 5% vegetative inoculum and grown under the same conditions as the seed flask. Samples of culture filtrate were assayed for inhibitor action against the β-lactamase of *Escherichia coli* JT4. Optimum activity was obtained after 3 days. The results are shown in Table.1. A zone of clavulanic acid at $R_f$ 0.46 was seen when the culture filtrate was examined by the paper chromatographic method previously described. The increase in size of the zone paralleled the increase in the β-lactamase inhibitor assay.

*Streptomyces clavuligerus* was also cultivated in 2 liter shaken flasks containing 400 ml s. of medium (Production stage) using the same medium and cultural conditions as described earlier in this Example. In these larger vessels, growth of the organism was slower and optimum 62-lactamase inhibitory activity was achieved 7–9 days after inoculation with the vegetative seed. The results are also shown in Table 1.

TABLE 1

β-Lactamase Inhibiting Activity of *Streptomyces clavuligerus* Grown in 500 ml. and 2000 ml. Flasks % Inhibition of Escherichia coli β-lactamase at a final dilution of 1/2500 of culture filtrate

| Fermentation Time (Days) | 500 ml. Shaken Flask | 2000 ml. Shaken Flask |
|---|---|---|
| 1 | 15 | — |
| 2 | 30 | — |
| 3 | 55 | — |
| 4 | 50 | 10 |
| 5 | 51 | 21 |
| 6 | 57 | 36 |
| 7 | — | 51 |
| 8 | — | 53 |
| 9 | — | 50 |

EXAMPLE 2

Cultivation of *Streptomyces clavuligerus*

A seed flask prepared as in Example 1 was used to inoculate 500 ml. conical flasks containing 100 ml. aliquots of the following medium in deionised water:

| | |
|---|---|
| Soluble Starch | 2% w/v |
| Glycerol | 0.3% w/v |
| Scotasol | 0.01% w/v |
| Arkasoy | 1% w/v |
| $FeSO_4.7H_2O$ | 0.01% w/v |

The medium was sterilized by autoclaving at 15 p.s.i. for 20 minutes and inoculated by the addition of the 5% vegetative seed stage. The flasks were shaken at 26° C. on a rotary shaker as in Example 1. Optimum titre of clavulonic acid was achieved between 3–5 days. A dilution of 1/2500 of the culture filtrate gave 60% inhibition in the β-lactamase inhibition assay. A zone of clavulanic acid was seen at $R_f$ 0.46 when using the paper chromatographic (bioautographic) method previously described. This zone increased in size in parallel with the increase of the activity in the β-lactamase inhibitor assay.

[Soluble starch supplied by British drug Houses, Ltd., Poole, U.K.;

Scotasol is dried distillers solubles supplied by Thomas Borthwich Ltd., 60 Wellington Street, Glasgow, UK;

Arkasoy is soya bean flour supplied by British Arkady Co., Old Trafford, Manchester, UK].

EXAMPLES 3

Cultivation of *Streptomyces clavuligerus*

A seed flask as produced in Example 1 was used to inoculate 500 ml. conical flasks containing 100 ml aliquots of the following medium prepared in deionised water and sterilised as previously described. The inoculum level was 5%.

| | |
|---|---|
| Dextrin | 2% w/v |
| Arkasoy | 1% w/v |
| Scotasol | 0.1% w/v |
| $FeSO_4\ 7H_2O$ | 0.01% w/v |

The inoculated flasks were shaken at 26° C. Optimum β-lactamase inhibitory activity was achieved between 3–5 days. The activity was similar to that achieved in Example 2.

[Dextrin is supplied by C P C (UK) Ltd., Trafford Park, Manchester, UK]

EXAMPLE 4

Cultivation of *Streptomyces clavuligerus*

The seed stage as described in Example 1 was used to inoculate 500 ml. conical flasks containing the following medium prepared in deionised water.

| | |
|---|---|
| Dextrose | 1% w/v |
| Soyabean Meal | 1% w/v |
| Scotasol | 0.05% w/v |
| $CsCO_3$ | 1% w/v |

These flasks were treated exactly as in previous Examples and cultured under identical conditions. β-lactamase inhibitory activity was produced between 3–5 days. Culture filtrate at a final dilution of 1/2500 gave 35–45% inhibition in the β-lactamase inhibition assay.

EXAMPLE 5

Cultivation of *Streptomyces clavuligerus*

β-lactamase inhibitory activity attributable to clavulanic acid was produced using the following medium with identical seed stage and cultivation conditions to Example 1.

| | |
|---|---|
| Glycerol | 2% w/v |
| Soyabean Meal | 1.5% w/v |
| Mg $SO_4$ | 0.1% w/v |
| $K_2HPO_4$ | 0.1% w/v |
| Medium prepared in deionised water | |

β-lactamase inhibitory activity reached a maximum level between 3–5 days and was of a similar order to that produced in Example 4.

EXAMPLE 6

Cultivation of *Streptomyces clavuligerus*

The following medium produced clavulanic acid when using the conditions and vegetative seed inoculum as described in Example 1.

| | |
|---|---|
| Glucose | 2% |
| Lab Lemco (Oxoid) | 1% |

-continued

| | |
|---|---|
| Oxoid Yeast Extract | 0.3% |
| CaCO₃ | 0.3% |
| Medium prepared in deionised water. | |

Optimum titres were achieved in 3–5 days and a 1/2500 dilution of the culture filtrate gave 35–45% inhibition in the β-lactamase enzyme inhibition assay.

EXAMPLE 7

Cultivation of *Streptomyces clavuligerus*

As in Examples 4, 5 and 6 the following medium produced 35–45% inhibition (1/2500 dilution) in the β-lactamase assay at the optimum titre which is reached 3–5 days after inoculation. All conditions were as previously described.

| | |
|---|---|
| Glucose | 2% w/v |
| Arkasoy | 1% w/v |
| CaCo₃ | 0.02% w/v |
| CoCl₂.6H₂O | 0.0001% w/v |
| Medium prepared in deionised water | |

EXAMPLE 8

Cultivation of *Streptomyces clavuligerus*

The following production stage medium when used under standard cultivation conditions as described in previous Examples produced 20–30% inhibition at 1/2500 dilution in the β-lactamase assay between 3–5 days after inoculation. Using the paper chromatographic method previously described, a zone of clavulanic acid was seen at $R_f$ 0.46 when culture filtrate was examined.

| | |
|---|---|
| Scotasol | 2% |
| Oxiod Yeast Extract | 1% |
| Medium prepared in tap water | |
| Final pH 7.0 | |

EXAMPLE 9

Cultivation of *Streptomyces clavuligerus*

Under standard cultivation conditions, the following medium produced clavulanic acid 3–5 days after inoculation with the vegetative seed. A 1/2500 dilution of the culture gave 20–30% inhibition in the β-lactamase inhibition assay.

| | g/l |
|---|---|
| Glucerol | 15 |
| Sucrose | 20 |
| Proline | 2.5 |
| Monosodium Glutamate | 1.5 |
| NaCl | 5.0 |
| K₂HPO₄ | 2.0 |
| CaCl₂ | 0.4 |
| MnCl₂4H₂O | 0.1 |

-continued

| | g/l |
|---|---|
| FeCl₃6H₂O | 9.1 |
| ZnCl₂ | 0.05 |
| MgSO₄7H₂O | 1.0 |
| Medium prepared in deionised water | |
| Final pH 7.1 | |

EXAMPLE 10

Cultivation of *Streptomyces clavuligerus*

A stock Yeatex/glucose agar slope was used to inoculate a Yeatex/glucose agar slope in a Roux bottle by making a mycelium/spore suspension in sterile water. The Roux bottle slope was incubated at 26° C. for 10 days. To this slope 100 mls. of sterile water was added and a mycelial suspension prepared. This was used to inoculate 50 liter of steam sterilised seed medium of the following composition in tap water.

| | |
|---|---|
| Oxoid Malt Extract | 1% w/v |
| Oxbid Bacteriological Peptone | 1% w/v |
| Clyceroi | 1% w/v |
| 10% Pluronic L81 Antifoam in Soyabean Oil | 0.05% w/v |

[Pluronic supplied by Jacobs and Van den Berg UK Ltd., 231 The Vale, London, W3 containing a polypropylene-polyethylene block polymer, and Soyabean Oil supplied by British Oil and Cake Mills Ltd., Stoneferry Road, Hull, U.K.].

The medium was contained in a 90 liter stainless steel baffled fermenter, agitated by a 5" vaned disc impeller at 240 r.p.m. Sterile air was supplied at 50 l/min and the tank incubated at 26° C.

After 72 hours, the seed fermenter was used to inoculate 150 liter of the same medium using a 5% v/v addition by sterile transfer. This production stage medium was contained in a 300 L stainless steel, fully baffled fermenter agitated by a 8½" vaned disc impeller at 210 r.p.m. Sterile air was supplied at 150 l/min. The fermentation was maintained at 26° C. Antifoam was added when required in 10 ml shots (10% Pluronic L81 in soyabean oil). Samples were removed for β-lactamase inhibition assay at regular intervals. The fermenter was harvested between 4–5 days at the optimum level of β-lactamase inhibitory activity (Table 2).

TABLE 2

β-Lactamase Inhibitory Activity of Samples of Culture Filtrate taken from a 300 liter Fermentation of *Streptomyces Clavuligerus*

| Fermentation Time (days) | % Inhibition in β-lactamase Inhibition Assay at a Final Dilution of 1/2500 |
|---|---|
| 1.0 | 12 |
| 1.5 | 20 |
| 2.0 | 31 |
| 2.5 | 36 |
| 3.0 | 50 |
| 3.5 | 54 |
| 4.0 | 51 |
| 4.5 | 56 |
| 5.0 | 55 |

EXAMPLE 11

Cultivation of *Streptomyces clavuligerus*

The seed fermenter was run exactly as described in Example 10 using the same medium.

After 72 hours, the seed fermenter was used to give a 5% v/v vegetative inoculum into a 300 liter stainless steel fully baffled fermenter containing 150 liter of steam sterilised medium agitated by an 8½ inch vaned disc impeller at 210 r.p.m. Sterile air was supplied at 150 l/min. The fermentation was maintained at 26° C. Antifoam was added when required in 10 ml. shots (10% Pluronic L81 in soya bean oil).

The medium used in the productions stage was as described in Example 3 with the addition of 0.05% v/v of 10% Pluronic L81/soyabean oil antifoam prior to sterilisation.

The β-lactamase inhibitory activity of fermentation samples was similar to those of Example 10 (see Table 2). Paper chromatographic examination revealed a zone of clavulanic acid at $R_f$ 0.46 using the bioautographic (synergism) method previously described. The size of the clavulanic acid zone increased in parallel with the increase in the β-lactamase inhibitor assay.

EXAMPLE 12

Cultivation of *Streptymyces clavuligerus*

100 mls of sterile water was added to a sporing culture which had been grown on Bennetts agar in a Roux bottle for 10 days at 26° C. A mycelium/spore suspension was produced and used to inoculate 75 liters of steam sterilised medium of the following composition in tap water.

| | |
|---|---|
| Dextrin | 2% W/V |
| Arkasoy '50' | 1% W/V |
| 10% Pluronic L81 in soyabean oil | 0.03% V/V |
| The pH of the medium was adjusted to 7.0 | |

The pH of the medium was adjusted to 7.0

The medium was contained in a 100 liter stainless steel baffled fermenter, agitated by a 7½" vaned disc impeller at 140 rpm. Sterile air was supplied at 75 l/minute and the tank incubated for 72 hours at 26° C.

The contents of the seed fermenter were used to inoculate 1500 liters of steam sterilised medium of the following composition in tap water.

| | |
|---|---|
| Arkasoy '50' | 1.5% W/V |
| Glycerol | 1.0% W/V |
| $KH_2PO_4$ | 0.1% W/V |
| 10% Pluronic L81 in soyabean oil | 0.2% V/V |
| The pH of the medium was adjusted to 7.0 | |

The pH of the medium was adjusted to 7.0

The medium was contained in a 2000 liter stainless steel fully baffled fermenter agitated by two 19" vaned disc impellers at 106 r.p.m.

Sterile air was supplied at 1200 liters per minute. antifoam was added in 25 ml amounts as required. (10% Pluronic L81 in soyabean oil). The fermentation was controlled at 26° C. until a maximum yield of clavulanic acid was obtained between 3–5 days when 200–300 µg/ml of clavulanic acid were produced.

EXAMPLE 13

Cultivation of *Streptomyces clavuligerus*

Inoculum was produced in a seed flask as previously described, but using the medium described in Example 3 (with pH of the medium adjusted to 7.0). This was used to inoculate 500 ml conical flasks containing 100 ml aliquots of the following medium prepared in deionised water and sterilised. The inoculum level was 5%.

| | |
|---|---|
| Prichem P224 | 1% W/V |
| Arkasoy '50' | 1.5% W/V |
| $KH_2PO_4$ | 0.1% W/V |
| The pH of the medium was adjusted to 7.0 | |

The inoculated flasks were shaken at 26° C. and optimum β-lactamase inhibitory activity was achieved between 3–5 days. Levels of 300–500 µg/ml of clavulanic acid were achieved.

Prichem P224 is a triglyceride supplied by Prices Limited, Bromborough, Bebington, Wirral, Cheshire, U.K.

Prichem P.224 is based on oleic acid (65%), palmitic acid (11%) and other similar acids.

EXAMPLE 14

Isolation of Crude Clavulanic Acid Sodium Salt

Harvested culture liquor produced as described in Example 10 was clarified by continuous flow centrifugation and the mycelium discarded. From 150 liter of fermentation liquor 120 liter of clarified culture fluid was obtained. This filtrate gave 58% inhibition in the β-lactamase inhibition assay at 1/2500. The filtrate was chilled to 5° C. and 40 liter of n-butanol added. The mixture was stirred and 25% $H_2SO_4$ added until the pH was 2.0. The acidified mixture was stirred for a further 10 mins. before separating the phases by centrifugation. The aqueous phase was discarded. To the n-butanol extract 0.5% of Norit GSX carbon was added and the mixture stirred for 15 minutes. The carbon was discarded after removal by filtration using a diatomaceus earth as a filter aid. To the n-butanol a ¼ volume of deionised water was added and the mixture stirred while adding 20% NaOH solution until the pH had equilibrated at 7.0. The phases were separated by centrifugation and the n-butanol phase discarded. The aqueous phase was concentrated under reduced vacuum to 800 ml. and then freeze dried. This yielded 35 g. of a crude solid preparation of clavulanic acid with an $I_{50}$ of 1.3 µg/ml in the β-lactamase inhibition assay. This solid preparation was stored dry at −20° C. while awaiting further purification.

EXAMPLE 15

Isolation of Crude Clavulanic Acid Sodium Salt

One liter of culture filtrate giving 53% inhibition at 1/2500 in the β-lactamase inhibition assay and obtained as described in Example 12 was percolated down a 1 inch diameter×6 inch column of Permutit Isopore resin FF 1P (SRA 62) in the Cl⁻ form [supplied by Permutit Co. Ltd., 632–652 London Road, Isleworth, Middlesex, U.K.]. The culture filtrate was followed by 300 ml. of distilled water to wash the column. Elution of the active β-lactamase inhibitor was achieved with 0.2M Nacl solution. Fractions (20 ml.) were collected and assayed at a 1/2500 final dilution in the β-lactamase inhibition assay. Active fractions were combined and concentrated under vacuum to 20 ml. This solution was desalted by gel exclusion chromatography on a Biorad Biogel P2 column 1½ inches in diameter with a gel bed of 16 inches and eluted with 1% n-butanol in water. [Biogel P2 is supplied by Bio Rad Laboratories, 32nd and Griffin Ave., Richmond, Calif., U.S.A.]. The active fractions, as determined by the β-lactamase inhibition assay, were combined. Sodium chloride eluted after clavulanic acid and was detected using silver nitrate solution. The combined active fractions were concentrated and freeze dried.

One liter of culture filtrate after the above treatment yielded 0.45 g. of a crude solid preparation of clavulanic acid having an $I_{50}$ of 0.92 µg/ml.

This solid was stored at −20° C. while awaiting further purification.

EXAMPLE 16

Isolation of Crude Clavulanic Sodium Salt

Culture filtrate containing 300 µg/ml of clavulanic acid is acidified using an in-line mixer system, extracted with n-butanol and clavulanic acid is back extracted into water at neutral pH.

Chilled culture filtrate (5–10° C.) was pumped to an in-line mixer at the inlet of which, enough 6% (v/v) nitric acid was added to maintain an outlet pH of 2.0±0.1. The acidified filtrate was passed at 4.1/min through a glycol cooled plate heat exchanger (A.P.V. Ltd.) to maintain a temperature between 2–5°. the pH was monitored in a flow cell before passing into a three stage counter current separator (Westfalia Separator Ltd., Model EG 1006).

Chilled water saturated n-butanol (at about 5° C.) was pumped at 3 l/min into the counter current separator.

The aqueous outlet from the counter current separator was run to waste. Entrained water was removed from the butanol outflow of the counter current separator using a liquid/liquid centrifugal separator. (Alfa Laval Ltd. Model 3024X-G). The butanol was collected in a stainless steel vessel fitted with a cooling jacket in which it was stored at about 5° C.

From the vessel, 40 l aliquots were removed and thoroughly mixed with 2 l of chilled water (5° C.), saturated with n-butanol. The pH of this mixture was adjusted to pH 6.8±0.1 using 20% sodium hydroxide solution.

This aqueous extract/butanol mixture was fed to a liquid/liquid centrifugal separator (Sharples Centrifuge Ltd. Model M35PY-5 PH) at a pumped rate of 2 k/min.

From 1800 l of culture filtrate, 90 l of aqueous phase was recovered, containing 39% of the clavulanic acid present in the culture filtrate.

15 l of the aqueous extract was adjusted from 2%, to 8%, total solids by the addition of 60 g sodium chloride per liter, and spray dried (Anhydro, Copenhagen, Type Lab S 1). The conditions used were: Feed rate 2 l/hr Atomizer voltage 170 v; Heater setting 6–7; Inlet temp 150° C.; Outlet temp 80° C.

The dried product, total weight 1 kg., contained 62% of the clavulanic acid present in the feedstock.

The remaining 75 l of aqueous extract was concentrated by ultrafiltration (De Danske Sukkerfabrikker. Laboratory Module, Membrane Type 900). The operating procedure was to re-circulate the retentate from a stainless steel tank, fitted with a cooling system, with the outlet valve set so as to give a differential pressure across the 40 membranes of 25 atmospheres. The temperature was maintained at 2–5° C. and the pH at 6.8±0.1 by addition of 2N hydrochloric acid, as necessary. The volume was reduced to 34 l which contained 72% of the clavulanic acid present in the feedstock.

The aqueous concentrate was stored at about 5° C., adjusted to 8% solids, and spray dried as above. The dried material contained 75% of the clavulanic acid present in the feedstock to the spray drier.

the total spray dried product, from the 90 l of aqueous extract contained 69.4 g of clavulanic acid which was 72% of the clavulanic acid in the spray drying feedstock and 21% of the clavulanic acid present in the 1800 l of culture filtrate.

EXAMPLE 17

Partial Purification of Crude Clavulanic Acid

Crude clavulanic acid preparations obtained as described in Example 15 were purified by ion exchange chromatography. Eighteen grams of material prepared as described in Example 15 having an $I_{50}$ value of 1.3 µg/ml (final concentration) were dissolved in 25 ml. of distilled water and applied to a 1½"×16" bed of Permutit FF 1P (SRA 62) resin in the chloride form. The column was eluted with a sodium chloride gradient formed by gravity feeding 0.5M sodium chloride into a mixing reservoir containing 1 liter of distilled water which in turn fed the chromatographic column. 10 ml. cuts were collected and β-lactamase inhibitory activity assayed using a 1/2500 dilution of the fractions. Activity was eluted after a main band of colour between fractions 24 and 30. the active fractions were combined and concentrated to 30 ml.

This solution was desalted using a 2"×18" bed of Biorad Biogel P2 and eluting with 1% n-butanol in water. The 20 ml. fractions were assayed for clavulanic acid content using the β-lactamase inhibition assay. The fractions were also spotted onto paper strips and sprayed with either the Ehrlich or the triphenyltetrazolium spray reagents described in Description 3. β-lactamase inhibitory activity correlated with the pink or red spots respectively produced by these reagents. Active cuts were combined, excluding those containing sodium chloride and concentrated under vacuum to dryness. This yielded 520 mg. of partially purified clavulanic acid sodium salt with an $I_{50}$ of 0.2 µg/ml in the standard β-lactamase inhibitor assay.

Thin layer chromatography (silica gel) of this clavulanic acid preparation gave the following $R_f$ values: n-butanol/ethanol/water 4:1:5 v/v top phase $R_f$ 0.37; n-butanol/acetic acid/water 12:3:5 v/v $R_f$ 0.44; isopropanol/water 7:3 v/v $R_f$ 0.78. The zones were detected by spraying with Ehrlich's reagent. 6-Aminopenicillanic run as a marker and detected with the same spray had $R_f$ values of 0.38; 0.39 and 0.77 respectively.

EXAMPLE 18

Partial Purification of Clavulanic Acid Sodium Salt

Culture filtrate produced as described in Example 12 was solvent extracted as in Example 14 to give a solid preparation which was further purified by ion exchange chromatography using Whatman diethylaminoethyl cellulose DE 52. This solid (10 g.) was dissolved in 20 ml. of distilled water and applied to a 1½"×20" column of DE 52 cellulose previously equilibrated with 0.01M sodium phosphate buffer pH 7.5 The column was eluted with a NaCl gradient. 0.1M Nacl in 0.01M sodium phosphate buffer pH 7.5 was fed into a mixing chamber containing 1 liter of 0.01M phosphate buffer pH 7.5 which in turn was connected to the column. Fractions (10 ml.) were collected and these were assayed for β-lactamase inhibitory activity at a dilution of 1/2500. The fractions were also examined for antibacterial activity by the hole-in-plate assay method using nutrient agar plates seeded with *Klebsiella aerogenes*. The fractions having the highest β-lactamase inhibitory activity and giving zones of inhibition in the hole-in-plate assay were combined, concentrated and then desalted on a Biorad Biogel P2 column. These fractions were shown to contain clavulanic acid by paper and thin layer chromatograph.

EXAMPLE 19

Isolation of Solid Clavulanic Acid Sodium Salt

A partially purified solid preparation of clavulanic acid (500 mg) prepared as in Example 17 was loaded onto a Whatman microcrystalline CC.31 cellulose column with 1"×20" bed size. The chromatographic solvent was n-butanol/ethanol/water 4:1:5 v/v, top phase. The column was run at 4° C. and 4 ml. fractions collected. Fractions were tested for the presence of clavulanic acid by spotting onto filter paper and spraying with the Ehrlich (pink spot) or triphenyltetrazolium (red spot) spray reagents. These spot tests were confirmed by β-lactamase inhibition assays at a 1/1250 dilution. Active fractions were combined and dried under vacuum on a rotary evaporator. The solid was dissolved in a small volume of distilled water and freeze dried. A white solid preparation of the sodium salt of clavulanic acid was obtained (40 mg) having an $I_{50}$ of 0.08 µg/ml in the β-lactamase inhibition assay.

EXAMPLE 20

Isolation of Solid Clavulanic Acid Sodium Salt

Concentrated back extract (6 l) (from ultrafiltration in Example 16) containing 10 g of clavulanic acid as determined by the β-lactamase inhibition assay of Description 1. This was percolated at 1 l/hr onto a 2"×24" column of Permutit Zerolit FF 1 P SRA 62 anion exchange resin in the chloride form. The column was then washed with 2 l of deionized water prior to elution with a sodium chloride gradient. The gradient was formed by a reservour containing 4 l of 1.4 m NaCl feeding a stirred reservoir containing 4 l of 0.7 Nacl which in turn was connected to a stirred reservoir containing 4 l of deionized water which was connected via a pump to the column. The column was eluted at 2.5 ml/min and 25 ml fractions collected. Fractions were assayed by the β-lactamase inhibition assay.

Active fractions (nos. 140–230) were combined and vacuum evaporated to near dryness. Ethanol (500 mls) was then added and the solid filtered off after vigorous shaking. The ethanol extract was then vacuum evaporated to dryness on a rotary avaporator and redissolved in deionized water (40 mls). This was loaded onto a 4"×24" column of Biorad Biogel $P_2$ and eluted with a 1% n-butanol solution. Fractions were collected (25 ml) and assayed for β-lactamase inhibitory activity at a 1/2500 final dilution. Tests for sodium chloride content on 1/25 dilutions of the fractions were made using silver nitrate solution. Those fractions containing clavulanic acid free of sodium chloride were combined, concentrated by evaporation of the solvent under reduced pressure to 20 mls and then freeze dried. This yielded 4.8 g of the sodium salt of clavulanic acid. ($I_{50}$ about 0.06 µg/ml)

EXAMPLE 21

Preparation of an Ester of Clavulanic Acid (Methyl Ester)

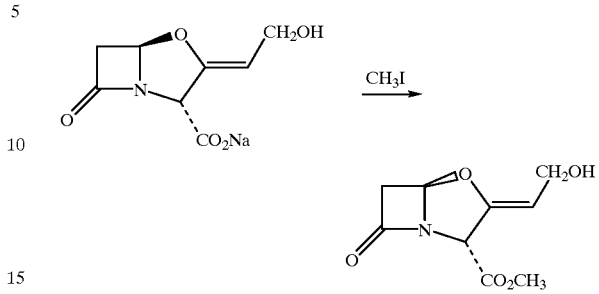

19.8 mg. of the sodium salt of clavulanic acid was dissolved in 0.5 ml. dry dimethylformamide and treated with 0.25 ml. methyl iodide. After standing at room temperature for 1.5 hours under anhydrous conditions, the solvents were removed in vacuo. The residue was purified by P.L.C. on silica gel (Kieselgel 60F254 supplied by E. Merck, Darmstadt, Germany) eluting with ethyl acetate to give clavulanic acid methyl ester as a colourless oil ($R_f$ 0.38; red colour with triphenyltetrazolium chloride spray) which had the following properties:

Analysis: Found C 50.49 H 5.43 N 6.29 $C_9H_{11}NO_5$ Requires C50.70 H 5.20 N 6.57

λmax (Methanol): no absorption >215 nm

νmax (Film): 3300–3600 (Broad), 1800, 1750, 1695 $cm^{-1}$

Approximate 1st order N.M.R. ($CDCl_3$): 2.49 (broad s, 1, exchanged with $D_2O$), 3.05 (d, 1, J=17.5Hz), 3.54 (dd, 1, J=17.5Hz, $J_2$=2.5Hz), 3.84 (s, 3) 4.24 (d, 2, J=7Hz), 4.93 (dt, 1, J=7Hz, $J_2$=1.5Hz), 5.07 (d, 1, J=1.5Hz), 5.72 (d, 1, J=2.5Hz).

Molecular weight (mass spectrum): 213.0635.

Calculated for $C_9H_{11}NO_5$: 213.0637.

Thin layer chromatography of the methyl ester showed a single zone in each of the following solvent systems; butanol/ethanol/water 4:1:5 v/v top phase $R_f$ 0.75; isopropanol/water, 7:3 v/v $R_f$ 0.95; ethylacetate/ethylalcohol 8:2 v/v $R_f$ 0.87. The zones were detected by bioautography using *Klebsiella aerogenes* with added benzylpenicillin (synergism system).

EXAMPLE 22

Preparation of an Ester of Clavulanic Acid (p-nitrobenzyl ester)

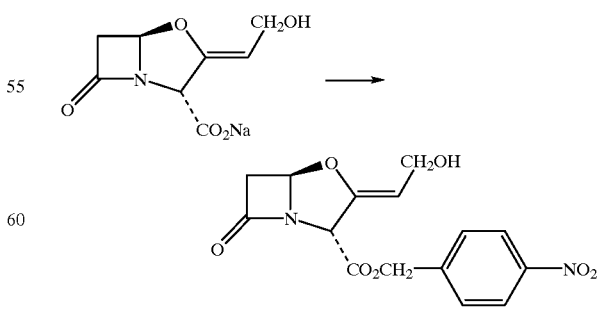

Treatment of the sodium salt of clavulanic acid with p-nitrobenzyl bromide in dry DMF gave, after P.L.C., a colourless oil which crystallised from chloroform—ether to give to p-nitrobenzyl ester of clavulanic acid as white feathery needles, m.p. 111–112° C., which on recrystallisation had a mp of 117.5–118° C.

EXAMPLE 23

Preparation of an Ester of Clavulanic Acid (Benzyl Ester)

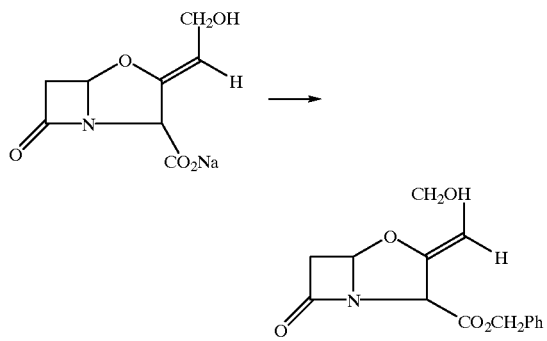

Impure 3-(β-hydroxyethylidine)-7-oxo-4-oxa-1-azabicyclo [3,2,0]heptane-2-carboxylic acid sodium salt (thought to be roughly 55 mg. of pure material) in dry dimethylformamide (0.64 ml.) was treated with benzyl bromide (0.18 ml.). The solution was kept at room temperature (approx. 17–18° C.) for 3 hours under anhydrous conditions. The reaction mixture was fractionated on silica gel, eluting with ethyl acetate, to give in substantially pure form the benzyl ester of 3-(β-hydroxyethylidine)-7-oxo-4-oxa-1-azabicyclo [3,2,0]heptane-2-carboxylic acid 63 mg.) as a colourless oil. i.r. (film) 1800, 1745, 1695 cm$^{-1}$; n.m.r. (CDCl$_3$), 2.25 (s, 1, exchangeable with D$_2$O), 3.05 (d,1, J=17Hz), 3.51 (dd, 1, J=17Hz, J$_2$=2.5Hz), 4.24 (d, 2, J=7.5Hz), 4.92 (dt, 1, J=7.5Hz, J$_2$=1.5Hz), 5.15 (d, 1, J=1.5Hz), 5.24 (s,2), 5.71 (d, 1, J=2.5Hz), 7.45 δ (s,5).

EXAMPLE 24

Preparation of the Benzyl Ester of Clavulanic Acid from Crude Extracts of the Fulture Filtrate of *S. clavuligerus*

Culture filtrate 20 l. obtained as described in Example 10 was vacuum evaporated using a climbing film evaporator to 5 l. The concentrate was then freeze dried using an Edwards E.F.6 shelf freeze drier manufactured by Edwards High Vacuum Ltd. The 300 g. of solid so obtained contained 3 g. of sodium Clavulanic acid as determined by the enzyme inhibition assay. The solid was suspended in 900 ml. of dry dimethylformamide and 150 ml. of benzyl bromide was added. The mixture was stirred for 2 hours at room temperature and then diluted with 1 l. of ethyl acetate. The reaction mixture was filtered and the filtrate concentrated to as low a volume as was possible. The oily residue was extracted with a further 1 l. of ethyl acetate and the extract filtered. The filtrate was again concentrated and the resulting oily residue loaded onto a 3"×14" silica gel column (Biogel Biosil A 100 mesh) in cyclohexane. The column was eluted with cyclohexane to remove benzyl bromide and the solvent was then changed to ethyl acetate and 20 ml. fractions collected. Fractions were tested for the presence of the benzyl ester of clavulanic acid by spotting onto glass backed silica gel t.l.c. plates (Merck precoated silica gel 60 F 254) and spraying with 2,3,5-triphenyl-tetrazolium chloride (TTC) spray reagent. Fractions giving intense red spots with this reagent were further examined by t.l.c. on silica gel plates using chloroform-ethyl acetate 8:2 as the solvent and spraying the developed plates with TTC spray. The benzyl ester of clavulanic acid runs at R$_f$ 0.31 at 22° C. Fractions containing this ester were combined and concentrated to 15 ml. and this solution was further chromatographed on a 1½"×16" silica gel column (Merck silica gel H, type 60) with chloroform/ethyl acetate 8:2 as the solvent. 15 ml. fractions were collected and tested for the benzyl ester as described above. Those fractions containing the ester were concentrated to 8 ml. and finally purified by column chromatography on a 1"×16" silica gel column (Merck silica gel H, type 60) with ethyl acetate cyclohexane 8:2 as the solvent. Selected fractions were combined and vacuum evaporated to give pure benzyl ester as an oil, 160 mg.

EXAMPLE 25

Preparation of Clavulanic Acid Benzyl Ester

Spray dried solid (3.3 kg) containing 69.4 g of clavulanic acid as determined by enzyme inhibition assay was obtained as described in Example 16. The solid was slurried in 5.5 l. of dimethylformamide and 500 mls. of benzyl bromide added. After stirring at room temperature for 2 hours, 12 l. of ethyl acetate were added and the solids removed by filtration. The filtrate was vacuum evaporated to an oily residue (212 g). The residue was loaded onto a column containing a 4"×13" bed of silica gel (Hopkins & Williams MFC) in cyclohexane. The column was eluted with 12 l. of cyclohexane to remove excess benzyl bromide. The eluent was then changed to ethyl acetate and 500 ml. fractions collected. These were tested for benzyl clavulanate content by spotting onto silican gel t.l.c. plates (Merck precoated silica gel 60 F 254) and spraying with 2,3,5 triphenyltetrazolium chloride (TTC) spray reagent. Fractions giving intense red spots were further examined by t.l.c. on silica gel with chloroform/ethyl acetate 8:2 as the solvent and spraying the developed plates with T T C spray. Fractions 5–13 contained the bulk of the ester, and these were combined and vacuum concentrated to an oil (79.3 g). This preparation was then chromatographed on a 4"×18" column of silica gel (Merck silica gel H type 60) with chloroform/ethyl acetate 8:2 as the solvent. Fractions were selected as described above and yielded on concentration 45.9 g. of oil which was of 62% purity as adjudged by NMR spectroscopy.

This product was finally chromatographed on a 2¾"×18" column of Sephadex LH 20 in cyclohexane/chloroform 1:1. After selection of fractions and concentration a colourless oil (27.6 g) was obtained which proved to be 95% pure benzyl ester of clavulanic acid as determined by NMR spectroscopic examination.

(Sephadex LH20 is a hydroxypropyl derivative of Sephadex Q25 supplied by Pharmacia Great Britain, 75 Uxbridge Road, London, W.5, U.K.).

EXAMPLE 26

Preparation of Clavulanic Acid Benzyl Ester

Culture filtrate (150 l) pH 7.0 contained 16.2 g. of clavulanic acid (sodium salt) as determined by the enzyme inhibition assay. This filtrate was stirred with 5 kg. of Amberlyst A.26 anion exchange resin in the chloride form (Rohm & Hass Company, Philadelphia, USA) for 1 hour at room temperature. The resin was then filtered and the filtrate reassayed, showing that 6.4 g of clavulanic acid had been removed. The resin was washed with 20 l. of deionised water followed by 20 l. of acetone and 10 l. of dimethyl formamide (DMF). After refiltering the resin was suspended in 2.3 l. of DMF/0.2 M NaI. To this was added 200 mls. of benzyl bromide and the suspension stirred thoroughly. After standing at room temperature for 16 hours, ethyl acetate (2 l) was added, and the resin then filtered, further washings (Ethyl acetate) of the resin were combined with the filtrate. The extract was then concentrated to a small volume and chromatographed on 3"×18" silica gel column (Merck silica gel H type 60) with ethyl acetate/cyclohexane 8:2 as the solvent. Fractions containing benzyl clavulanate were selected by spotting onto silcia gel t.l.c. plates and spraying with TTC reagent as described previously (Example 24). Those selected were concentrated to 20 mls and then chromatographed on a 1½"×18" silica gel column (Merck silica gel H type 60) with chloroform/ethyl acetate 8:2 as the solvent. Selected fractions were combined and evaporated to a colourless oil (440 mgs) which was 90% benzyl clavulanate as determined by NMR spectroscopy.

EXAMPLE 27

Preparation of the Benzyl Ester of Clavulanic Acid from Crude Extracts of the Culture Filtrate of *S. clavuligerus*

An aliquot of aqueous back extract of the butanol extract of culture filtrate obtained as described in Example 14 was freeze dried using an Edwards chamber drier. A 24 g. portion of the solid obtained contained 0.96 g. of sodium clavulanic acid as determined by the enzyme inhibition assay. This solid was suspended in 75 ml. of dry dimethylformamide and 75 ml. of benzyl bromide was added. The mixture was stirred for 2 hours at room temperature. The suspension was then diluted with 500 ml. of ethyl acetate and the mixture filtered. The filtrate was concentrated to an oily residue on a vacuum rotary evaporator. This residue was loaded onto a 2"×14" silica gel column (Biogel Biosil A.100 mesh) in cyclohexane. Benzyl bromide was eluted from the column and then the solvent was changed to ethyl acetate and 10 ml. fractions was collected. Fractions containing the benzyl ester of clavulanic acid were selected as in Example 24. Further purification was also achieved as described in Example 24 by column chromatography. This process yielded 220 mg. of pure benzyl ester.

EXAMPLE 28

Preparation of Clavulanic Acid Sodium Salt

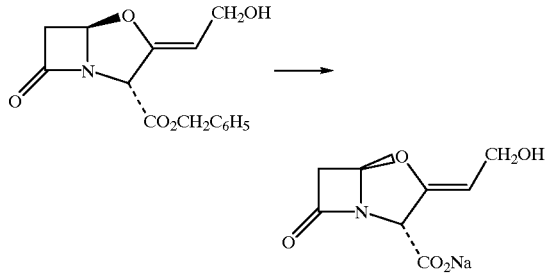

Substantially pure benzyl clavulanate (281 mg) in ethanol (25 ml.) containing sodium hydrogen carbonate (82 mg.) was hydrogenated over 10% Pd/C (90 mg.) for 25 minutes at room temperature and atmospheric pressure. The catalyst was filtered off, washed with water and ethanol, and the combined filtrates evaporated under reduced pressure at room temperature. The residual semi-solid was triturated with acetone, filtered and washed with ether to yield sodium clavulanate (135 mg.).

EXAMPLE 29

Hydrolysis of Clavulanic Acid Methyl Ester to Clavulanic Acid 2.17 mg. of clavulanic acid ester was dissolved in 0.1 ml. methanol and treated with 0.208 ml. sodium hydroxide solution (0.0482N). After 1 hour at room temperature, the reaction mixture contained several products. T.L.C. analysis indicated that one of the major components had an $R_f$ identical to that of the sodium salt of clavulanic acid; colour reactions and biological assay were consistent with this component being the sodium salt of clavulanic acid.

Slow conversion of the ester to clavulanic acid was seen when 1 mg/ml. of the compound was incubated at 37° C. in 0.05M phosphate buffer at pH 7. The reaction was followed by paper chromatography (bioautographic system). Using the butanol/ethanol/water system to follow the reaction over a period of 2 hours the zone of the methyl ester at $R_f$ 0.79 decreased in size as the zone of clavulanic acid at $R_f$ 0.12 increased.

EXAMPLE 30

Antibacterial Spectrum of Clavulanic Acid

The antibacterial activity of clavulanic acid sodium salt against a range of bacteria was determined using the microtitre method. Serial dilutions of clavulanic acid sodium salt in Oxoid sensitivity test broth contained in a microtitre plastic tray were inoculated with an overnight broth culture of each organism so that the final dilution of the inoculum was $0.5 \times 10^{-4}$. The cultures were incubated overnight and the points of bacterial growth recorded next morning by observing the turbidity of the culture. The results, expressed as approximate MIC values (minimum inhibitory concentration µg/ml.) are recorded in Table 3 which shows that the compound has a broad spectrum of antibacterial activity.

TABLE 3

ANTIBACTERIAL SPECTRUM OF CLAVULANIC ACID SODIUM SALT

| Bacterial Strain | Minimum Inhibitory Concentration µg/ml. |
|---|---|
| *Staphylococcus aureus* (Oxford H) | 7.5 |
| *Staphylococcus aureus* (Russell) | 7.5 |
| *Bacillus subtilis* | 62 |
| *Streptococcus faecalis* | >500 |
| *Streptococcus pyogenes* CN 10 | 125 |
| *Escherichia coli* NCTC 10418 | 31 |
| *Klebsiella aerogenes* | 31–62 |
| *Klebsiella oxytocum* | 62 |
| *Enterobacter aerogenes* T 624 | 31 |
| *Enterobacter cleacea* | 62 |
| *Acinetobacter anitratus* | 125 |
| *Providentia stuartii* | 125 |
| *Serratia marcescens* | 125 |
| *Proteus mirabilis* C977 | 62 |
| *Proteus vulgaris* W090 | 31 |
| *Salmonella typhimurium* | 31 |
| *Shigella sonnei* | 62 |
| *Pseudomonas aeruginosa* A | 500 |

EXAMPLE 31

Examples of β-Lactamase Inhibition by Clavulanic Acid Sodium Salt

Clavulanic acid progressively and irreversibly inhibits the β-lactamase of *Escherichia coli*. The method of Description 1 shows that the other β-lactamases shown in Table 4 are also inhibited by clavulanic acid.

TABLE 4

INHIBITION OF β-LACTAMASES BY CLAVULANIC ACID

| Source of β-lactamase | Approximate $I_{50}$ Value Relative to *Escherichia coli* JT 4 = 1 |
|---|---|
| *Staphylococcus aureus* (Russell) | 1.0 |
| *Escherichia coli* JT4 | 1.0 |
| *Escheriahia coli* B11 | 2.0 |
| *Klebsiella aerogenes* A | 0.6 |
| *Pseudomonas aeruginosa* 1822 (R factor) | 5.0 |
| *Pseudomonas dalgleish* | 0.1 |

With penicillin G as substrate the $I_{50}$ of clavulanic acid sodium salt against the β-lactamase of *Staph. aureus* (Russell) is approximately 0.06 μg/ml.

EXAMPLE 32

Examples of Activity of Clavulanic Acid Methyl Ester

Tests for antibacterial activity in broth showed clavulanic acid methyl ester to have broad spectrum activity but of a lower order than shown by clavulanic acid. It was not clear whether this activity was the activity of the compound itself or of clavulanic acid liberated by slow aqueous hydrolysis of the ester. Clavulanic acid methyl ester showed marked antibacterial synergism in combination with ampicillin or cephaloridine against bacteria resistant to these antibiotics. Thus, the minimum inhibitory concentration (M.I.C.) for ampicillin against *Staphylococcus aureus* (Russell) was reduced from 500 μg/ml. to <0.4 in the presence of 1.0 μg/ml. clavulanic acid methyl ester. The M.I.C. for cephaloridine was reduced from 1.5 μg/ml. to <0.03 μg/ml. in the presence of 1 μg=/ml. of clavulanic acid methyl ester. The M.I.C. for ampicillin against *Proteus mirabilis* C889 was reduced from 500 μg/ml. to 31 μg/ml. in the presence of 5 μg/ml. clavulanic acid methyl ester.

EXAMPLE 33

Preparation Pivaloyloxymethyl Clavulanate

To a stirred solution of bromomethyl pivalate (C. 37 g) in dry dimethylformamide (5 ml) was added sodium clavulanate (0.49 g). After 2 hrs. at room temperature the reaction mixture was treated with ethyl acetate (20 ml), cyclohexane (10 ml) and water (20 ml). The mixture separated into two layers and the non-aqueous layer was separated, washed with water (20 ml) and dried over sodium sulphate. The dried solution was evaporated to leave the required product as a pale yellow oil. (500 mg). N.m.r. (CDCl$_3$), 1.26 (s,9), 3.13 (d, 1, J=17Hz), 3.62 (dd, 1, J=17Hz, J$_1$=2.5Hz, 4.3 (d, 2, J=7.5Hz), 5.0 (dt, 1, J=7.5Hz, J$_2$=1.5Hz), 5.16 (d, 1, J=1.5Hz), 5.79 (d, 1, J=2.5Hz), 5.92 δ (s,2); i.r. (liquid film), λ β-lactam C.O 1800 cm$^{-1}$, ester C=O 1760 cm$^{-1}$.

EXAMPLE 34

Preparation of Clavulanic Acid Phthalide Esters

To a stirred solution of 3-bromophthalide (0.43 g) in dry dimethylformamide (5 ml) was added sodium clavulanate (0.5 g) and the solution was left at room temperature for 2 hours. The solution was treated with ethyl acetate (20 ml), cyclohexane (10 ml) and water (30 ml) and shaken thoroughly. The non-aqueous layer was washed with water (20 ml), dried (Na$_2$SO$_4$) and evaporated to yield a pale yellow gum. The two diasteromeric esters were separated using high pressure liquid chromatography on a 40 cm×10 mm column of silica gel (Merckosorb SI 60, 5μ) eluting with ethyl acetate at a flow rate of 3 ml/min.

The first phthalide ester (retention time 7.15 min) crystallised from ethyl acetate as needles, mp 102°, and had the following i.r. (nujol mull) ν β-lactam C=O 1790 cm$^{-1}$ ester C=O 1755 cm$^{-1}$ n.m.r. (CD$_3$COCD$_3$): 3.14 (d, 1, J=17.5Hz) 3.76 (dd, 1, J,=17.5Hz), J$_2$=2.5Hz), 4.25 (d, 2, J=7.5Hz), 5.0 (dt, 1, J$_1$=7.5Hz), J$_2$=1.5Hz), 5.4 (s, 1, J=1.5Hz) 5.82 (d, 1, J=2.5Hz), 7.7 (s,1), 8.06δ (m,4); M.wt (mass spectrometry: 331.0696 corresponds to C$_{16}$H$_{13}$NO$_7$ (calc. 331.0692). The second diasterioisomer (retention time 8.85 min) had the following i.r. (CH$_2$Cl$_2$solution) ν β-lactam C=O 1800 cm$^{-1}$, ester C=O 1780 cm$^{-1}$; nmr (CDCl$_3$) 2.42 (broad S, 1, exchangeable with D$_2$O), 3.12 (d, 1, J=18Hz), 3.60 (dd, 1, J$_1$=18Hz, J$_2$=2.5Hz), 4.30 (d, 2, J=7.5Hz), 5.0 (dt, 1, J$_1$=7.5Hz, J$_2$=1.5Hz), 5.12 (d, 1, J=1.5Hz), 5.76 (d, 1, J=2.5Hz), 7.52 (S,1), 7.85δ (m, 4).

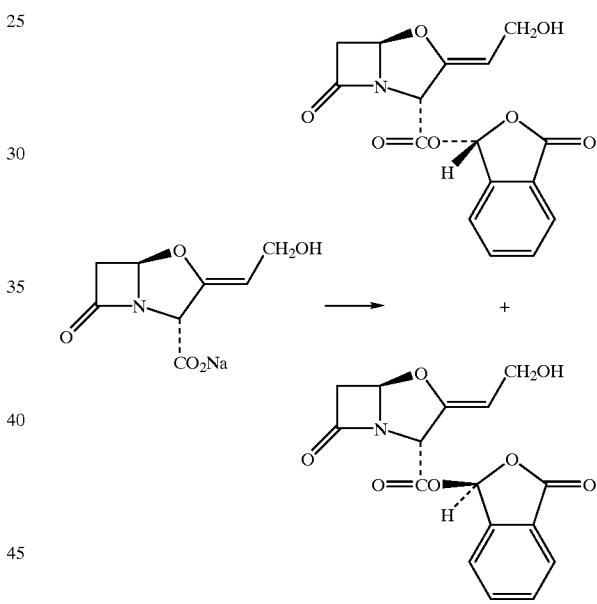

EXAMPLE 35

Preparation of Nonyl Clavulanate

Sodium clavulanate (44 mg) in dry dimethylformamide (2 ml) was treated with nonyl iodide (76 mg) and left at room temperature for 2 hours. The solution was evaporated and the residue fractionated on silica gel, eluting with ethyl acetate-hexane (2:1) to give the product as an oil; i.r. (film) 1800, 1745, 1690 cm$^{-1}$. M.wt. (mass spectromethyl)= 325.1890 which corresponds to C$_{17}$H$_{27}$NO$_5$. (calc. 325.1889).

EXAMPLE 36

Preparation of Clavulanic Acid

Benzyl clavulanate (100 mgs) in ethanol (5 ml) was hydrogenated over 10% Pd/C (30 mgs) for 45 minutes at ambient temperature and atmospheric pressure. The catalyst was filtered, washed with ethanol and the combined filtrates were evaporated in vacuo to give clavulanic acid as an unstable, viscous oil (58 mgs). N.m.r. ($C_5D_5N$): 3.05 (d, 1, J=18Hz), 3.60 (dd, 1, $J_1$=18Hz, $J_2$=2.5Hz), 4.75 (d, 2, J=7.5Hz), 5.58 (t, 1, J=7.5Hz), 5.66 (S,1), 6.0δ (d, 1, J=2.5Hz).

EXAMPLE 37

Preparation of Methyl Clavulanate

Clavulanic acid (130 mgs) in ethanol (10 ml) was treated with excess diazomethane in ether. After 2 minutes at room temperature the reaction was shown (t l c) to be complete. The solution was evaporated in vacuo and the residue purified by chromatography on silica gel, eluting with ethyl acetate. The fractions containing methyl clavulanate were combined and evaporated to give a clear oil (104 mgs).

EXAMPLE 38

Preparation of Methyl Clavulanate

Clavulanic acid (200 mgs) in acetonitrile (5 ml) was cooled and stirred at 0°. Methanol (0.5 ml) and then dicyclohexyldicarbodiimide (206 mg.) were added and the reaction mixture was stirred at room temperature overnight. The suspension was filtered and the filtrate evaporated in vacuo to give crude methyl clavulanate. The crude product was purified by chromatography on silica gel, eluting with ethyl acetate, to give a clear oil (140 mg).

EXAMPLE 39

Preparation of Phenyl Clavulanate

Clavulanic acid (100 mg) in acetonitrile (5 ml) was cooled and stirred at 0°. To the solution was added phenol (0.94 g) and dicyclohexyldicarbodiimide (100 mg) and the reaction mixture was stirred at room temperature overnight. The suspension was filtered and the filtrate evaporated. The residue was fractionated on silica gel, eluting with ethyl acetate-hexane (1:1) to give phenyl clavulanate (70 mg). I.r (film) 1800, 1770, 1690 cm$^{-1}$. N.m.r. (CDCl$_3$) 2.18 (broad s,1), 3.06 (dd, 1, J=17Hz, $J_2$=0.9Hz), 3.54 (dd, 1, $J_1$=17Hz, $J_2$=2.6Hz), 4.29 (d, 2, J=7.5Hz), 5.1 (dt, 1, $J_1$=7.5Hz, $J_2$=1.5Hz) 5.29 (d, 1, J=1.5Hz), 5.76 (dd, 1, $J_1$=2.6Hz, $J_2$=0.9Hz), 7.35δ (m,5). M.wt. (mass spectrometry)= 275.0777 which corresponds to $C_{14}H_{13}NO_5$ (calc. 275.0794).

EXAMPLE 40

Preparation of 2,2,2-Trichloroethyl Clavulanate

Sodium clavulanate (221 mgs) was suspended in dry tetrahydrofuran (5 mls) and stirred at 0°. Trichloroethylchloroformate (211 mg) in dry tetrahydrofuran (1 ml) was added to the above suspension over 20 minutes. The mixture was allowed to reach room temperature and stirred overnight. The suspension was filtered and the filtrate evaporated in vacuo. The residue was chromatographed on silica gel eluting with ethyl acetate—hexane (2:1) to give the required product as an oil. i.r (film) 1800, 1760, 1690 cm$^{-1}$. n.m.r. (CDCl$_3$) 1.56 (broad S,1), 3.07 (dd, 1, $J_1$=17.5Hz, $J_2$=0.7Hz), 3.56 (dd, 1, $J_1$=17.5Hz, $J_2$=2.5Hz), 4.24 (d, 2, J=7.5Hz), 4.69 (d, 1, J=12Hz), 4.92 (d, 1, J=12Hz), 5.02 (dt, 1, $J_1$=7.5Hz, $J_2$=1.3Hz), 5.19 (d, 1, J=1.3Hz), 5.73δ (dd, 1, $J_1$=2.5Hz, $J_2$=0.7Hz). M.wt. (mass spectrometry)=328.9621 which corresponds to $C_{10}H_{10}NO_5Cl_3$ (calculated 328.9625).

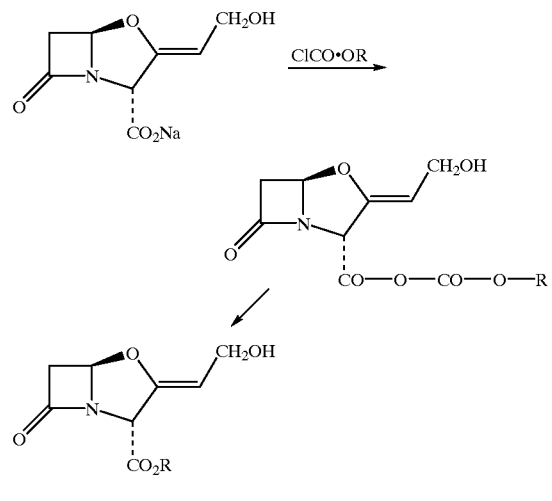

R = $CH_2Cl_3$

EXAMPLE 41

Preparation of Sodium Clavulanate

Benzyl clavulanate (840 mgs) in ethanol (30 ml) and water (5 ml) was hydrogenated over 10% Pd/C (267 mgs) and sodium bicarbonate (244 mgs) for 25 minutes at room temperature and atmospheric pressure. The catalyst was filtered, washed with water and ethanol and the combined filtrates were evaporated in vacuo. The product crystallised from a water-acetone mixture as microneedles (565 mgs). Recrystallisation from water-acetone gave needles which, after drying over $P_2O_5$ in vacuo for 24 hours gave the following analysis: C 41.01, 40.86; H 3.77, 3.64; N 5.68, 5.51; i.r. (KBr disc) 1785, 1700, 1620 cm$^{-1}$; Nmr ($D_2O$) 3.06 (d, 1, J=18.5Hz), 3.57 (dd, 1, $J_1$=18.5Hz, $J_2$=2.5Hz), 4.15 (d, 2, J=8Hz), 5.3 (HOD), 4.9 (m), 5.71 (d, 1, J=2.5Hz).

EXAMPLE 42

Antibacterial Synergism between Ampicillin and Clavulanic Acid Sodium Salt

The minimum inhibitory concentration (M.I.C. values) of ampicillin, clavulanic acid sodium salt and ampicillin in the presence of 1 μg/ml. clavulanic acid sodium salt were determined for a range of β-lactamase producing bacteria. The organisms were inoculated into Oxoid sensitivity test broth located in small wells in a plastic tray and containing separate concentration gradients of ampicillin, clavulanic acid sodium salt or ampicillin plus 1 μg/ml. clavulanic acid sodium salt (microtitre method). The final dilution of the overnight broth inoculum was 0.5×10$^{-2}$. The tray was incubated at 37° C. overnight and a record made next morning of the end points of bacterial growth. The M.I.C. values in μg/ml. are recorded in Table 5 which reveals that the synergist at the low concentration of 1 μg/ml. markedly enhances the antibacterial activity of ampicillin against certain gram+ve and gram−ve bacteria. The mechanism of this synergism is likely to involve inhibition of ampicillin destroying β-lactamase enzymes but the existence of other mechanisms cannot be excluded.

Similar results to those shown in Table 5 were obtained when ampicillin was replaced by amoxycillin or by the phthalidyl ester of ampicillin.

TABLE 5

ANTIBACTERIAL SYNERGISM BETWEEN AMPICILLIN AND CLAVULANIC ACID SODIUM SALT

| | Minimum Inhibitory Concentrations μg/ml | | |
|---|---|---|---|
| Bacterial strain | Clavulanic acid sodium salt | Ampicillin | Ampicillin in presence of 1 μg/ml clavulanic acid sodium salt |
| Escheriachia coli NCTC 10481 | 31 | 1.8 | <0.4 |
| Escherichia coli B 11 | 62 | >500 | 125 |
| Klebsiella aerogenes A | 31 | 125 | <0.4 |
| Klebsiella sp 62 | 31 | 125 | <0.4 |
| Enterohacter cloacae | 62 | 250 | 62 |
| Serratia marcescens | 125 | >500 | 62 |
| Staphylococcus aureus (Russell) | 15 | 500 | <0.4 |
| Staphylococcus | 62 | 250 | 7.5 |

EXAMPLE 43

Antibacterial Synergysm between Cephaloridine and Clavulanic Acid Sodium Salt

The minimum inhibitory concentrations of cephaloridine, clavulanic acid sodium salt and cephaloridine in the presence of 5 μg/ml clavulanic acid sodium salt were determined by the method described in Example 42. The results in Table 6 show that synergism can be obtained between clavulanic acid sodium salt and cephaloridine particularly for the β-lactamase producing strain of Staphylococcus aureus (Russell).

TABLE 6

ANTIBACTERIAL SYNERGISM BETWEEN CEPHALORIDINE AND CLAVULANIC ACID SODIUM SALT

| | Minimum Inhibitory Concentrations μg/ml. | | |
|---|---|---|---|
| Bacterial strain | Clavulanic acid sodium salt | Cephaloridine | Cephaloridine in presence of 5 μg/ml clavulanic acid sodium salt |
| Proteus mirabilis 899 | >500* | 62 | 7.5 |
| Staphylococcus aureus (Russell) | 15 | 3.1 | <0.03+ |
| Staphylococcus aureus | 62 | 15 | 3.7 |

*Tailing Point
+Same value obtained when synergist added at 1 μg/ml instead of 5 μg/ml.

EXAMPLE 44

Antibacterial Synergism between Clavulanic Acid Sodium Salt and Various Penicillins The results presented in Table 7 were obtained by the method described in Example 42.

TABLE 7

ANTIBACTERIAL SYNERGISM BETWEEN CLAVULANIC ACID SODIUM SALT AND VARIOUS PENICILLINS AGAINST STRAINS OF KLEBSIELLA AEROGENES

| | Amoxycillin | | Carbenicillin* | | Benzylpenicillin | |
|---|---|---|---|---|---|---|
| Strain | Alone | +5 μg/ml. synergist | Alone | +5 μg/ml. synergist | Alone | +5 μg/ml. synergist |
| A | 500 | 0.97 | 500 | 7.8 | 250 | 7.8 |
| E 70 | 500 | 3.9 | 500 | 15 | 500 | 15.6 |
| 62 | 250 | 15.6 | 125 | 7.8 | 250 | 15.6 |

*Similar results observed when carbenicillin replaced by carbenicillin phenyl α-ester or ticacillin.

EXAMPLE 45

Antibacterial Synergism between Ampicillin and Esters of Clavulanic Acid

The results presented in Table 8 were obtained by the method described in Example 42.

TABLE 8

ANTIBACTERIAL SYNERGISM BETWEEN AMPICILLIN AND ESTERS OF CLAVULANIC ACID AGAINST STRAINS OF KLEBSIELLA AEROGENES

| Strain | Ampicillin Alone | Ampicillin + 5 μg/ml of Methyl Ester of clavulanic acid | Ampicillin + 5 μg/ml of Benzyl Ester of clavulanic acid |
|---|---|---|---|
| A | 500 | 1.9 | 1.9 |
| E 70 | 500 | 3.9 | 3.9 |
| 62 | 500 | 3.9 | 3.9 |

Neither clavulanic acid methyl ester nor clavulanic acid benzyl ester inhibited the growth of the test organisms at a concentration of 100 μg/ml.

EXAMPLE 46

Antibacterial Activity of Clavulanic Acid Ester

The method of Example 30 but using a dilution of 1/100 of overnight broth, the MIC values in Table 9 were obtained for certain esters of clavulanic acid against a number of organisms:

TABLE 9

ANTIBACTERIAL ACTIVITY OF CLAVULANIC AICD ESTERS

| | MIC of Ester of Clavulanic Acid | | | | MIC* of |
|---|---|---|---|---|---|
| Organism | Benzyl ester | Nonyl ester | Pivaloyloxy-methyl ester | Phthalidyl ester | calvulanic acid sodium salt |
| Bacillus subtilis A | 250 | 31 | 62 | 125 | 62 |
| Staph. aureus Oxford | 62 | 31 | 31 | 31 | 15 |
| Staph. aureus Russell | 125 | 31 | 62 | 15 | 15 |

TABLE 9-continued

ANTIBACTERIAL ACTIVITY OF CLAVULANIC AICD ESTERS

| Organism | MIC of Ester of Clavulanic Acid | | | | MIC* of calvulanic acid sodium salt |
|---|---|---|---|---|---|
| | Benzyl ester | Nonyl ester | Pivaloyloxy-methyl ester | Phtha-lidyl ester | |
| *Escherichia coli* 10418 | 125 | 250 | 125 | 125 | 125 |

*The MIC of clavulanic acid sodium salt is included for comparison; the high MIC values (if compared to those of Example 30) are due to the heavy inocula used.

EXAMPLE 47

Extraction of Clavulanic Acid using Liquid Ion Exchange Resin

Culture filtrate (200 ml, obtained in a similar manner to Example 3 but using a medium containing 0.1% v/v $KH_2PO_4$ instead of 0.01% $FeSO_4.7H_2O$) was extracted with Amberlite* $LA2^+(Cl^-$ form, 15% v/v in methylisobutyl ketone, 66 ml) for 30 minutes at 5° C.

The phases were separated by centrifugation (1660 g, 20 minutes). The solvent phase (60 ml) was recovered by pipette and divided into four equal portions. Each portion was extracted by stirring at 5° C. for 20 minutes with ¼ volume (3.75 ml) aqueous extractant as indicated in the table below. The resulting mixture was centrifuged (1660 g, 15 minutes). 3.6 ml. aqueous phase was recovered from each extraction.

| Sample | Volume (ml) | Clavulanic acid concentration ($\mu$g ml$^{-1}$) | Clavulanic acid (mg) |
|---|---|---|---|
| clarified brew | 200 | 128 | 25.4 |
| extracted brew | 200 | 15 | 3.0 |
| M NaCl extract | 3.6 | 305 | 1.1 |
| 2M NaCl extract | 3.6 | 598 | 2.5 |
| M NaNO$_3$ extract | 3.6 | 638 | 2.3 |
| 2M NaNO$_3$ extract | 3.6 | 758 | 2.73 |

The result obtained with 2M NANO$_3$ represents a recovery of 43% from clarified brew.
*Amberlite LA2 is obtainable from Rohm and Haas (UK) Ltd. Croydon.

EXAMPLE 48

Extraction of Clavulanic Acid using Liquid Ion Exchange Resin

Clarified brew (47 liters, obtained as in Example 12) was extracted with Amberlite LA2 (acetate form, 15% v/v in methylisobutyl ketone, 12.5 liters) by stirring for 1 hour at 17° C. After adding octan-1-ol (500 ml) the phases were separated in a continuous flow centrifuge yielding 9.2 liters solvent phase, which was then stirred at 5° C. for 1½ hours with molar sodium nitrate (2.3 liters). The mixture was separated by continuous flow centrifugation yielding 2.4 liters aqueous phase (including water used for displacement purposes). Aqueous phase pH (initially 8.0) was adjusted to 7.0 with concentrated hydrochloric acid.

| Sample | Volume (l) | clavulanic acid concentration ($\mu$g ml$^{-1}$) | clavulanic acid (mg) |
|---|---|---|---|
| clarified brew | 47 | 147 | 6862 |
| extracted brew | 47 | 19 | 893 |
| M NaNO$_3$ extract | 2.4 | 1638 | 3931 |

Extraction efficiency from clarified brew to sodium nitrate extract is 57%.

What is claimed is:

1. A solid pharmaceutically acceptable salt of clavulanic acid.

* * * * *

(12) REEXAMINATION CERTIFICATE (4466th)

United States Patent
Cole et al.

(10) Number: US 6,031,093 C1
(45) Certificate Issued: Oct. 16, 2001

(54) SOLID SALTS OF CLAVULANIC ACID

(75) Inventors: Martin Cole, Dorking; Thomas T Howarth, Rudwick; Christopher Reading, Southwater, all of (GB)

(73) Assignee: SmithKline Beecham, p l c, King of Prussia, PA (US)

Reexamination Request:
No. 90/005,745, Jun. 13, 2000

Reexamination Certificate for:
Patent No.: 6,031,093
Issued: Feb. 29, 2000
Appl. No.: 08/417,628
Filed: Apr. 6, 1995

Related U.S. Application Data

(63) Continuation of application No. 07/749,482, filed on Aug. 15, 1991, which is a continuation of application No. 07/210,339, filed on Jun. 23, 1988, now abandoned, which is a continuation of application No. 05/569,007, filed on Apr. 17, 1975, now abandoned.

(51) Int. Cl.[7] ............... C07D 503/195; A61D 31/42; C12P 17/18
(52) U.S. Cl. ......................................... 540/349
(58) Field of Search .............. 514/210.06; 540/347, 540/348, 349

(56) References Cited

U.S. PATENT DOCUMENTS 4,529,720   7/1985   Cole et al. ..................... 514/191

*Primary Examiner*—Richard L. Raymond

(57) ABSTRACT

A new antibacterially active agent has been isolated from Streptomyces clavuligerus. This new compound which is designated clavulanic acid has the formula (I):

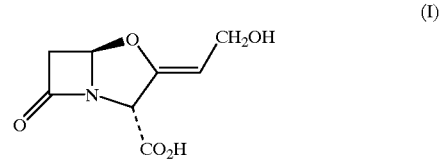

In addition to being a broad spectrum antibiotic of medium potency, clavulanic acid and its salts and esters have the ability to enhance the effectiveness of β-lactam antibiotics against many β-lactamase producing bacteria.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

\* \* \* \* \*